(12) United States Patent
Kelleher et al.

(10) Patent No.: US 9,358,267 B2
(45) Date of Patent: *Jun. 7, 2016

(54) HIGH PURITY LIPOPEPTIDES

(71) Applicant: Cubist Pharmaceuticals LLC, Lucerne (CH)

(72) Inventors: Thomas J. Kelleher, Thousand Oaks, CA (US); Jan-Ji Lai, Westborough, MA (US); Joseph P. DeCourcey, Boston, MA (US); Paul D. Lynch, Arlington, MA (US); Maurizio Zenoni, Milan (IT); Auro R. Tagliani, Pavia (IT)

(73) Assignee: Cubist Pharmaceuticals LLC, Lucerne (CH)

( * ) Notice: Subject to any disclaimer, the term of this patent is extended or adjusted under 35 U.S.C. 154(b) by 0 days.

This patent is subject to a terminal disclaimer.

(21) Appl. No.: 14/475,319

(22) Filed: Sep. 2, 2014

(65) Prior Publication Data

US 2014/0371135 A1  Dec. 18, 2014

Related U.S. Application Data

(60) Continuation of application No. 13/918,083, filed on Jun. 14, 2013, now Pat. No. 8,853,357, which is a continuation of application No. 13/398,219, filed on Feb. 16, 2012, now Pat. No. 8,604,164, which is a continuation of application No. 12/888,233, filed on Sep. 22, 2010, now Pat. No. 8,129,342, which is a continuation of application No. 11/739,180, filed on Apr. 24, 2007, now Pat. No. 8,058,238, which is a continuation of application No. 10/747,485, filed on Dec. 29, 2003, now abandoned, which is a division of application No. 09/735,191, filed on Nov. 28, 2000, now Pat. No. 6,696,412.

(60) Provisional application No. 60/177,170, filed on Jan. 20, 2000.

(51) Int. Cl.

| | |
|---|---|
| *A01N 37/18* | (2006.01) |
| *A61K 38/04* | (2006.01) |
| *A61K 38/12* | (2006.01) |
| *A61K 38/10* | (2006.01) |
| *C07K 5/097* | (2006.01) |
| *C07K 7/08* | (2006.01) |
| *C07K 1/14* | (2006.01) |

(52) U.S. Cl.
CPC .............. *A61K 38/12* (2013.01); *A61K 38/10* (2013.01); *C07K 1/145* (2013.01); *C07K 5/0821* (2013.01); *C07K 7/08* (2013.01); *Y10S 435/886* (2013.01)

(58) Field of Classification Search
None
See application file for complete search history.

(56) References Cited

U.S. PATENT DOCUMENTS

| | | | |
|---|---|---|---|
| 4,331,594 A | 5/1982 | Hamill et al. | |
| 4,439,425 A | 3/1984 | Tarcsay et al. | |
| 4,482,487 A | 11/1984 | Abbott et al. | |
| 4,524,135 A | 6/1985 | Abbott et al. | |
| 4,537,717 A | 8/1985 | Abbott et al. | |
| RE32,310 E | 12/1986 | Debono | |
| RE32,311 E | 12/1986 | Debono | |
| RE32,333 E | 1/1987 | Hamill et al. | |
| RE32,455 E | 7/1987 | Hamill et al. | |
| 4,800,157 A | 1/1989 | Eaton et al. | |
| 4,874,843 A | 10/1989 | Baker et al. | |
| 4,882,164 A | 11/1989 | Ferro | |
| 4,885,243 A | 12/1989 | Huber et al. | |
| 5,271,935 A | 12/1993 | Franco et al. | |
| 5,336,756 A | 8/1994 | Schwartz et al. | |
| 5,387,670 A | 2/1995 | Roy et al. | |
| 5,573,936 A | 11/1996 | Kreuzman et al. | |
| 5,629,288 A | 5/1997 | Lattrell et al. | |
| 5,912,226 A | 6/1999 | Baker et al. | |
| 5,955,509 A | 9/1999 | Webber et al. | |
| 6,194,383 B1 | 2/2001 | Hammann et al. | |

(Continued)

FOREIGN PATENT DOCUMENTS

| | | |
|---|---|---|
| EP | 0095295 | 11/1983 |
| EP | 0178152 | 4/1986 |

(Continued)

OTHER PUBLICATIONS

Cubist Pharmaceuticals Proposed Findings of Fact and Conclusions of Law Pre-Trial Order for Civil Action No. 12-367-GMS (Feb. 14, 2014).

(Continued)

*Primary Examiner* — Marcela M Cordero Garcia
(74) *Attorney, Agent, or Firm* — Dianne Pecoraro; Mark R. Daniel

(57) ABSTRACT

The invention discloses highly purified daptomycin and to pharmaceutical compositions comprising this compound. The invention discloses a method of purifying daptomycin comprising the sequential steps of anion exchange chromatography, hydrophobic interaction chromatography and anion exchange chromatography. The invention also discloses a method of purifying daptomycin by modified buffer enhanced anion exchange chromatography. The invention also discloses an improved method for producing daptomycin by fermentation of *Streptomyces roseosporus*. The invention also discloses high pressure liquid chromatography methods for analysis of daptomycin purity. The invention also discloses lipopeptide micelles and methods of making the micelles. The invention also discloses methods of using lipopeptide micelles for purifying lipopeptide antibiotics, such as daptomycin. The invention also discloses using lipopeptide micelles therapeutically.

32 Claims, 11 Drawing Sheets

(56) References Cited

U.S. PATENT DOCUMENTS

| | | | |
|---|---|---|---|
| 6,468,967 | B1 | 10/2002 | Oleson et al. |
| 6,696,412 | B1 | 2/2004 | Kelleher et al. |
| 6,794,490 | B2 | 9/2004 | Hill et al. |
| 6,852,689 | B2 | 2/2005 | Oleson et al. |
| RE39,071 | E | 4/2006 | Baker et al. |
| 8,003,673 | B2 | 8/2011 | Alder et al. |
| 8,058,238 | B2 | 11/2011 | Kelleher et al. |
| 8,129,342 | B2 | 3/2012 | Kelleher et al. |
| 8,309,061 | B2 | 11/2012 | Chaudry |
| 8,431,539 | B2 | 4/2013 | Palepu et al. |
| 8,853,357 | B2 * | 10/2014 | Kelleher et al. ............... 530/317 |
| 2002/0111311 | A1 | 8/2002 | Govardhan et al. |
| 2003/0045484 | A1 | 3/2003 | Keith et al. |
| 2003/0045678 | A1 | 3/2003 | Keith et al. |
| 2005/0009747 | A1 | 1/2005 | Kelleher et al. |
| 2005/0027113 | A1 | 2/2005 | Miao et al. |
| 2006/0014674 | A1 | 1/2006 | Keith et al. |
| 2007/0128694 | A1 | 6/2007 | Baltz et al. |
| 2009/0197799 | A1 | 8/2009 | Keith et al. |
| 2010/0041589 | A2 | 2/2010 | Keith et al. |
| 2012/0149062 | A1 | 6/2012 | Kelleher et al. |
| 2012/0270772 | A1 | 10/2012 | O'Connor |

FOREIGN PATENT DOCUMENTS

| | | |
|---|---|---|
| EP | 0294990 | 12/1988 |
| EP | 0386951 | 9/1990 |
| EP | 0511866 | 11/1992 |
| EP | 0521408 | 1/1993 |
| EP | 0629636 | 12/1994 |
| EP | 0337731 | 1/1997 |
| EP | 1252179 | 10/2002 |
| EP | 1115417 | 4/2006 |
| JP | 64047388 | 2/1989 |
| JP | 04224197 | 8/1992 |
| JP | 05239090 | 9/1993 |
| JP | 05271284 | 10/1993 |
| WO | WO9321207 | 10/1993 |
| WO | WO 96/36370 A1 | 11/1996 |
| WO | WO9822107 | 5/1998 |
| WO | WO9927954 | 6/1999 |
| WO | WO9927957 | 6/1999 |
| WO | WO9930728 | 6/1999 |
| WO | WO9940113 | 8/1999 |
| WO | WO9943700 | 9/1999 |
| WO | WO9955310 | 11/1999 |
| WO | WO0018419 | 4/2000 |
| WO | WO0144271 | 6/2001 |
| WO | WO0144272 | 6/2001 |
| WO | WO0144274 | 6/2001 |
| WO | WO0153330 | 7/2001 |
| WO | WO02059145 | 8/2002 |
| WO | WO02096936 | 12/2002 |
| WO | WO03063745 | 8/2003 |
| WO | WO2004104019 | 12/2004 |

OTHER PUBLICATIONS

Hospira Proposed Findings of Fact and Conclusions of Law Pre-Trial Order for Civil Action No. 12-367-GMS (Feb. 14, 2014).

Akins et al.; Bactericidal Activities of Two Saptomycin Regimens against Clinical Strains Glycopeptide Intermediate-Resistant *Staphylococcus aureus*, Vancomycin-Resistant Enterococcus faccium, and Methicillin-Resistant *Staphylococcus aureus* Isolates in an In Vitro Pharmacodynamic Model with Simulated Endocardial Vegetations; Antimicrobial Agents and Chemotherapy; 2001, vol. 45, pp. 454-459.

Akins et al., In Vitro Activities of Daptomycin, Arbekacin, Vancomycin, and Gentamicin Alone and/or in Combination against Glycopeptide Intermediate-Resistant *Staphylococcus aureus* in an Infection Model; Antimicrobial Agents and Chemotherapy; 2000, vol. 44, pp. 1925-1929.

Arbeit et al., The Safety and Efficacy of Daptomycin for the Treatment of Complicated Skin and Skin-Structure Infections; Clinical Infectious Diseases; 2004, vol. 38, pp. 1673-1681.

Auwera et al., Ex-vivo study of serum bactericidal titers and killing rates of daptomycin (L Y146032) combined or not combined with amikacin compared with those of vancomycin; Antimicrobial Agents and Chemotherapy; 1989, vol. 33, pp. 1783-1790.

Baltz, "Lipopeptide Antibiotics Produced by Streptomyces roseosporus and Streptomyces fradiae," Biotechnology of Antibiotics 1997, 2d ed.; pp. 415-435.

Barclay et al., What is the Evidence for Once-Daily Aminoglycoside Therapy; Clin. Pharmacokinetics. 1994, 27(i), pp. 32-48.

Barry et al., In vitro activities of daptomycin against 2,789 clinical isolates from 11 North American Medical Centers; Antimicrobial Agents and Chemotherapy; 2001, vol. 45, pp. 1919-1922.

Bayer et al., L Y146032 Compared with Penicillin Gin Experimental Aortic Valve Endocarditis Caused by Group G Streptococci, Antimicrobial Agents and Chemotherapy 1988, vol. 32, pp. 141-143.

Benoit et al. "Destruction and regeneration of skeletal muscle after treatment with a local anesthetic, bupivacaine (Marcaine®)," J Anal. 1970. vol. 107, pp. 547-556.

Benvenuto et al., Pharmacokinetics and Tolerability of Daptomycin at Doses up to 12 Milligrams per Kilogram of Body Weight Once Daily in Healthy Volunteers; Antimicrobial Agents and Chemotherapy; 2006, vol. 50, pp. 3245-3249.

Bingen et al., Bactericidal activity of Fancomycin, Daptomycin, Ampicillin and Aminoglycosides against Vancomycin-resistant Enterecoccus; J of Antimicrobial Chemotherapy; 1990; vol. 26, pp. 619-626.

BioTrends Research Group, *TreatmentTrends® : MRSA and Serious Gram-Positive Infections (US)* 2012.

Bryant et al., Effect of Abscess Milieu on Bactericidal Activity of IX146032 against Staphylococci; Eur. J. Clin. Microbiol,; 1987, vol. 16, pp. 186-188.

Caballero Granado et al.; Case-control Study of Risk Factors for the Development of Enterococcal Bacteremia; Eur. J. Olin. Microbial. Infect. Dis. 2001, vol. 20, pp. 83-90.

Caron et al,; Daptomycin or teicoplanin in combination with gentamicin for treatment of experimental endocarditis due to highly glycopeptide-resistant isolate of Enterococcus faecium; Antimicrobial Agents and Chemotherapy; 1992, vol. 36, pp. 2611-1616.

Carteret al., Protein Cystallization Using Incomplete Factorial Experiments; J. Biol. Chem., 1979, 1979, vol. 254, pp. 12219-12223.

Chaflari et al.; Efficacy and safety of daptomycin in the treatment of Gram-positive catheter-related bloodstream infections in cancer patients; Internation Journal of Antimicrobial Agents; 2010, vol. 36, pp. 182-186.

Chayen et al.; Recent advances in methodology for the crystallization of biological macromolecules; Journal of Crystal D Growth; 1999, pp. 649-655.

Cooper et al., "Enhanced Production of Surfactin from *Bacillus subtilis* by Continuous Product Removal and Metal Cation Additions," *Applied and Envtl. Microbiology*, 42 (3): 408-12 (1981).

Craig, "Once-daily versus multiple-daily dosing of aminoglycosides," J. Chemother.; 1995, vol. 7 (Suppl 2), pp. 47-52.

Crompton et al., Outcomes with daptomycin in the treatment of *Staphylococcus aureus* infections with a range of vancomycin MICs; Journal of Antimicrobial Chemotherapy; 2010, vol. 65, pp. 1784-1791.

Cubicin lable, Nov. 2011; 34 pages.

Cubicin.RTM. (daptomycin for injection) Label 1004, Sep. 2003.

Cubicin.RTM. (daptomycin for injection) Label 1004-1, Revised Aug. 2004.

Cubucin.RTM. (daptomycin for injection) Label 1004-2, Revised Jun. 2005.

Cubicin.RTM. (daptomycin for injection) Label 1004-10-1, Aug. 2010.

Cubicin.RTM. (daptomycin for injection) Label 1004-11, Nov. 2010.

Cui et al., Correlation between Reduced Daptomycin Susceptibility and Vancomycin Resistance in Vancomycin—Intermediate *Staphylococcus au reus*; Antimicrobial Agents and Chemotherapy; 2006, vol. 50, pp. 1079-1082.

(56) References Cited

OTHER PUBLICATIONS

Cubist Pharmaceuticals, Press Release, Feb. 5, 2008, Lexington, MA.
*Cubist Pharmaceutical, Inc.* v. *Hospira, Inc.*, No. 1 :12cv367 (D. Mass. Filed Mar. 21, 2012) (Def. Hospira, Inc. Preliminary Invalidity Contentions).
Cunha et al., Daptomycin resistance and treatment failure following vancomycin for methicillin-resistant *Staphylococcus aureus* (MRSA) mitral valve acute bacterial endocarditis (ABE); Eur. J. Clin. Microbiol. Infect. Dis.; 2009, vol. 28, pp. 831-833.
Davis et al., Daptomycin versus Vancomycin for Complicated Skin and Skin Structure Infections: Clinical and Economic Outcomes, Pharmacotherapy, 2007, vol. 27, pp. 1611-1618.
Debbia et al., In Vitro Activity of L Y146032 Alone and in Combination with Other Antibiotics against Gram-Positive Bacteria, Antimicrobial Agents and Chemotherapy, 1988, vol. 32, pp. 279-281.
Debono, et al., "A21978C, A Complex of New Acidic Peptide Antibiotics: Isolation, Chemistry, and Mass Spectral Structure Elucidation," The Journal of Antibiotics 1987, vol. XL (6), p. 761-77.
Debono et al., Enzymatic and Chemical Modifications of Lipopeptide Antibiotic A21978C: The Synthesis and Evaluation of Daptomycin (LY146032), 8. J. Antibiotics 1093 (1988).
Debruin, Michael F., Efficacy and safety of daptomycin for the treatment of bacteremia and serious infections due to gram-positive bacteria; 4th Decennial International Conference on Nosocomial and Healthcare-Associated Infections; Poster #594 P-S2-37 (Mar. 5-9, 2000), 14 pages.
(Decision Resources, *Antibiotic Market Opportunities Beyond the Hospital: Market Trends, Medical Practice, and Reimbursement of Outpatient Parenteral Antibiotic Therapy (OPAT): A Survey of Infectious Disease Specialists and Managed Care Organization Medical Directors* (2011)).
Desai et al., Microbial Production of Surfactants and Their Commercial Potential; Microbiology and Molecular Biology Reviews 1997, vol. 61, pp. 47-64.
DuCruix, et al., Crystallization of Nucleic acids and Proteins, A Practical Approach, 2d ed., 1999, pp. 92-95,4 pages.
Dvorchik et al., Daptomycin Pharmacokinetics and Safety following Administration of Escalating Doses Once Daily to Healthy Subjects; Antimicrobial Agents and Chemotherapy; 2003, vol. 47, pp. 1318-1323.
Ebert et al., Pharmacodynamics Properties of Antibiotics: Application to Drug Monitoring and Dosage Regimen Design; Infection Control and Hospital Epidemiology; 1990, 11(6), pp. 319-326.
Eliopoulos et al., In Vitro and In Vivo Activity of L Y146032, a New Cyclic Lipopeptide Antibiotic; Antimicrobial Agents and Chemotherapy 1986, vol. 30, pp. 532-535.
El-Mady et al., The Bactericidal Activity of Ampicillin, Daptomycin, and Vancomycin Against Ampicillin-Resistant Enteroccus faecium, Diagn. Micro. Inf. Dis., 1991, vol. 14, pp. 141-145.
Evdokimov et al., Overproduction, purification, crystallization and preliminary X-ray diffraction analysis of YopM, an essential virulence factor extruded by the plague bacterium Yersinia pestis, Acta Crystallographica, 2000, vol. 56, pp. 1676-1679.
Faruki et al., Effect of Calcium on In Vitro Activity of L Y146032 against Clostridium difficile; Antimicrobial Agents and Chemotherapy 1987, vol. 30, pp. 461-462.
Forward et al., Comparative activity of daptomycin and teicoplanin against enterococci isolated from blood and urine, Can. J, Infect. Dis., 1992, Vol, 3, pp. 173-178.
Fostel et al., "Emerging Novel Antifungal Agents," DDT; vol. 5; No. 1; Jan. 2000; pp. 25-35.
Fowler et al., Daptomycin versus Standard Therapy for Bacteremia and Endocarditis Caused by *Staphylococcus aureus*, The New England Journal of Medicine, 2006, vol. 355, pp. 653-665.
Freeman et al., Once-daily Dosing of Aminogiycosides: Review and Recommendations for Clinical Practice; J. Antimicr. Chemother, 1997, vol. 39, pp. 677-686.
1 Harrison's Principles of Internal Medicine (14th ed., Fauci A. et al., ed. McGraw-Hill, 1998).

Haworth et al.; *Staphylococcus aureus* ventriculitis treated with single-dose intraventricular vancomycin or daptomycin (L Y146032): bacterial and antibiotic kinetics in hydrocephalic rabbits; Antimicrobial Agents and Chemotherapy 1990. vol. 34. pp. 245-251.
Hodgkinson and Lowry, "Hydrophobic-interaction chromatography and anion-exchange chromatography in the presence of acetonitrile," *Biochem. J.*, 199: 619-27 (1981).
Horowitz et al., Isolation and Characterization of a Surfactant Produced by Bacillus Licheniformis 86; Journal of Industrial Microbiology 1990, vol. 6, pp. 243-248.
Jancarik et al., Sparse matrix sampling: a screening method for crystallization of proteins, J Appl. Cryst., 1991, vol. 24, pp. 409-411.
Janson et al., Protein Purification: Principles, High Resolution Methods, and Applications; Ch. 1: Introduction to Protein Purification; John Wiley & Sons, Inc., 1998; pp. 3-48, p. 80, and pp. 125-126.
Johnson et al., ICAA 1987, poster 161, 1 page.
Katz et al., A pilot study of high-dose short duration daptomycin for the treatment of patients with compiicated skin and skin structure infections caused by gram-positive bacteria, International Journal of Clinical Practice, 2008, pp. 1-10.
Kirsch, et al, "Kinetics of the Aspartyi Transpeptidation of Daptomycin, a Novel Lipopeptide Antibiotic," Pharmaceutical Research: 1989, vol. 6, p. 387-93
Koshino et al., "A New Cyclic Lipopeptide Antibiotic, Enamidonin" *J. of Antibiotics* 48(2):185-87 (1995).
Lakey and Ptak, "Fluorescence Indicates a Calcium-Dependent Interaction between the Lipopeptide Antibiotic LY146032 and Phospholipid Membranes," *Biochemistry 27*: 4639-45 (1998).
Lasic, Mixed Micellers in Drug Delivery; Nature 1992, vol. 355, pp. 279-282.
Lasic, Novel Applications of Liposomes; Trends in Biotechnology 1998, vol. 16, pp. 307-321.
Lee et al., Program and Abstracts of the ICAAC 1991, Abstract No. 865.
LeClercq et al.. Effects of Combinations of Beta-Lactams, Daptomycin, Gentamicin and Glycopeptides against Glycopeptide-Resistant Enterococci; Antimicrobial Agents and Chemotherapy, 1991, vol. 35, pp. 92-98.
Lin et al., General Approach for the Development of High-performance Liquid Chromatography Methods for Biosurfactant Analysis and Purification; Journal of Chromatography 1998, vol. 825, pp. 149-159.
Lin et al., "Recovery and Purification of the Lipopeptide Biosurfactant of Bacillus subtilis b Ultrafiltration," Biotechnology Techniques. 1997, vol. 11, p. 413-16.
Lin et al., "Structural and Immunological Characterization of a Biosurfactant Produced by *Bacillus licheniformis* JF-2," *Applied and Envtl. Microbiology*, 60(1): 31-38 (1994).
Lodish et al., Molecular Cell Biology (ed. by J. Darnell, H. Lodish, and D. Baltimore, Scientific American Books, Inc., New York: 1986), Chapter 3, p. 53.
Louie et al., Comparison of in vitro inhibitory and Bactericial Activities of Daptomycin (L Y 146032) and Four Reference Antibiotics, Singly and in Combination, against Gentamicin-Susceptible and High-Level-Gentamicin-Resistant Enterococci; Chemotherapy; 1993, Vol, 39, pp. 302-310.
Lowy, "Vancomycin intermediate and vancomycin-resistant *Staphylococcus aureus* infections," Wolters Kluwer Health, UpToDate (Jul. 23, 2013).
Luu et al., Treatment of Chronic Experimental *Staphylococcus aureus* Osteomyelitis with L Y 146032 and Vancomycin; Eur. J. Clin. Microbiol. Infect. Dis, 1989, vol. 8, pp. 562-563.
Mader et al., Comparative Evaluation of Daptomycin (L Y146032) and comycin in the Treatment of Experimental Methicillin-Resistant *Staphylococcus aureus* Osteomyelitis in Rabbits; Comparative Evaluation of Daptomycin Antimicrobial Agents and Chemotherapy, 1989, vol. 33, pp. 689-692.
Mariani et al., Development of decreased susceptibility to daptomycin and vancomycin in a *Staphylococcus aureus* strain during prolonged therapy; Journal of Antimicrobial Chemotherapy 2013, pp. 481-483.

(56) References Cited

OTHER PUBLICATIONS

Matthews et al., IDSA poster, 2001.

Mchenney et al., Molecular Cloning and Physical Mapping of the Daptomycin Gene Cluster from Streptomyces roseosporus; Journal of Bacteriology, 1998, vol. 180, pp. 143-151.

McKindley et al., "Drug Use in the Critically Ill Patient with Renal Dysfunction-Application of the DREM System," Infectious Diseases in Critical Care Medicine Biotechnology of Antibiotics (ed. B.A. Cunha, New York: Marcel Dekker, Inc., 1998) Chapter 41, pp. 781-801.

Miao et al., "Daptomycin biosynthesis in Streptomyces roseosporus: cloning and analysis of the gene cluster and revision of peptide stereochemistry," Microbiology 2005, vol. 151 (5), 1507-23.

Mobarakai et al., Bactercidal Activities of Peptide Antibiotics against Multidrug-Resistant Enterococcus faecium; Antimicrobial Agents and Chemotherapy; 1994. vol. 38, pp. 385-387.

Moise et al., Susceptibility relationship between vancomycin and daptomycin in *Staphylococcus aureus*: facts and assumptions; Lancet Infect: Dis. 2009, vol. 19, pp. 617-624.

Molloy, et al., Abstract, "Structure & Anhydro-Daptomycin and Iso-Daptomycin," ACS 200th Meeting, 1990.

Molloy, et al., Poster, "Structure & Anhydro-Daptomycin and Iso-Daptomycin," ACS 20th Meeting, 1990.

Morikawa et al., "A New Lipopeptide Biosurfactant Produced by *arthrobacter*sp. Strain MIS38," *J. of Bacteriology* 175(20):6459-66 (1993).

Mulligan et al., Recovery of Biosurfactants by Ultrafiltration; J. Chem. Tech. Biotechnology 1990, vol. 47, pp. 23-29.

Mutschler et al., Drug Actions: Basic Principles and Therapeutic Aspects; Ch. 2: Pharmacokinetics; Medpharm Scientific Publishers, Stuttgart, Germany (1995); p. 5, 47 pages.

Osman et al., "Tuning Micelles of a Bioactive Heptapeptide Biosurfactant via Extrinsically Induced Conformational Transition of Surfactin Assembly," *J. Peptide Sci.*, 4(7):449-58 (1998).

Pascual, et al., Effect of Polyurethane Catheters and Bacterial Biofilms on the In-Vitro Activity of Antimicrobials Against *Staphylococcus epidermidis*; Journal of Hospital Infection 1993, vol. 24, pp. 211-218.

Patel et al., An Association between Reduced Susceptibility to Daptomycin and Reduced Susceptibility to Vancomycin in *Staphylococcus aureus*; Ciinical Infectious Diseases: Correspondance to the Editor; Jun. 1, 2006, vol. 42, pp. 1652-1653.

Ramos et al., Comparison of Daptomycin, Vancomycin, and Ampicillin-Gentamicin for Treatment of Experimental Endocarditis Caused by Penicillin-Resistant Enterococci; Antimocrobial Agents and Chemotherapy 1992; vol. 36; pp. 1864-1869.

Remington: The Science and Practice of Pharmacy, (19th edition, Mack Publishing Company, 1985), pp. 539-551, 1529-1530, 1549-1550, and 1558.

Rotschader et al., "Therapeutic Update on Glycopeptide and Lipopeptide Antibiotics," Pharmacotherapy 1988, vol. 8, 211-19.

Sader et al., Nine-Hospital Study Comparing Broth Microdilution and Etest Method Results for Vaqncomycin and Daptomycin against Methicillin-Resistant *Staphylococcus aureus*; Antimicrobial Agents and Chemotherapy, 2009, vol. 53, pp. 3162-3165.

Sader et al., Update on the In Vitro Activity of Daptomycin Tested against 17,193 Gram-positive Bacteria Isolated from European Medical Centers (2005-2007); Journal of Chemotherapy 2009, vol. 21, pp. 500-506.

Sakoulas et al., Clinical Outcomes of Patients Receiving Daptomycin for the Treatment of *Staphylococcus aureus* Infections and Assessment of Clinical Factors for Daptomycin Failure: A Retrospective Cohort Study Tuilizing the Cubicin Outcomes Registry and Experience; Clinical Therapeutics. 2009, vol. 31, pp. 1936-1945.

Sapico et al., 146032, Alone and in Combination with Gentamicin, for the Treatment of Enterococcal Pyelonephritis in the Rat Model; Antimicrobial Agents and Chemotherapy 1988, vol. 32, pp. 81-83.

Schnellmann et al.; Cassarett and Donis Toxicology: The Basic Science of Poisons; Chapter 14: Toxic Responses of the Kidney; (5th ed.) (1996), pp. 491-514.

Schott, Colloidal Dispersions; Remington: The Science and Practice of Pharmacy; vol. 1, 19th Edition, 1995; pp. 252-277, Mack Publishing Company; Easton, Pennsylvania USA.

Selwyn, et al.; Infections (Excluding AIDS) of Injection Drug Users; Harrison's Principles of Internal Medicine; Fauci, et al. eds., 14th ed., McGraw-Hill, 1998, pp. 831-832, and 847.

Sexton D. et al., "The Use of Daptomycin, a Lipopeptide Antibiotic, in the Treatment of Gram Positive Infections in Man," Interscience Conference on Antimicrobial Agents and Chemotherapy 1988, Abstract No. 932.

Shaw, D.J., "Liquid-Gas and Liquid-Liquid Interfaces," Introduction to Colloid and Surface Chemistry, Butterworth-Heinemann Ltd., 1989, pp. 49-90.

Sievert et al., "Vancomycin-Resistant *Staphylococcus aureus* in the United States, 2002-2006." 46 Clin. Infect. Dis. 668 (2008).

Silva et al., In Vitro Activity of L Y146032 Against Gram-Positive Bacteria; Diagn. Microbiol. Infect. Dis., 1988, vol. 9, pp. 79-85.

Silverman et al., Inhibition of Daptomycin by Pulmonary Surfactant: In Vitro Modeling and Clinical Impact; The Journal of Infectious Disease; 2005, vol. 191, pp. 2149-2152.

Silverman et al., Resistance Studies with Daptomycin; Antimicrobial Agents and Chemotherapy; 2001, vol. 45, pp. 1799-1802.

Smith et al., *Emergence of Vancomycin Resistance in Staphylococcus aureus*, 340 N. Engl. J. Med. 493 (1999).

Snydman et al., Comparative In Virro Activities of Daptomycin and Vancomycin against Resistant Gram-Positive Pathogens; Antimicrobial Agents and Chemotherapy; 2000, vol. 44, pp. 3447-3450.

Steenbergen et al., Daptomycin: a lipopeptide antibiotic for the treatment of serious Gram-positive infections; Journal of Antimicrobial Chemotherapy, 2005, vol. 55, pp. 283-288

Sterling; "Membrane-Based System Combines Selective Separation with High-Volume Throughput," Genetic Engineering News; vol. 19; No. 20; Nov. 15, 1999; pp. 1, 34.

Stratton et al., Bactericidal Activity of Daptomycin (L Y146032) Compared with Those of Ciprofloxacin, Vancomycin, and Ampicillin against Enterococci as Determined by Kill-Kinetic Studies; Antimicrobial Agents and Chemotherapy 1987, vol. 31, pp. 1014-1016.

Supersaxo et al., "Mixed Micelles as Proliposomal. Lymphotropic Drug Carrier," Pharmaceutical Research 1991; vol. 8. pp. 1286-1291.

Sweadner et al., "Filter Removal of Endotoxin (Pyrogens) in Solution in Different States of Aggregation," Applied and Environmental Microbiology 1977; vol. 34, pp. 382-385.

Tally et al., Daptomycin: a novel agent for Gram-positive infections; Expert Opinion on Investigational Drugs; 1999, vol. 8, pp. 1223-1238.

Tenover et al., Characterisation of a *Staphylococcus au reus* strain with progressive loss of susceptibility to vancomycin and daptomycin during therapy; International Journal of Antimicrobial Agents; 2009, p. 564-68.

Thibault et al., Attenuation by Daptomycin of Gentamicin-Induced Experimental Nephrotoxicity; Antimicrobial Agents and Chemotherapy; 1994, vol. 38, pp. 1027-1035.

Thimon et al., "Surface-Active Properties of Antifungal Lipopeptides Produced by Bacillus Substillis," J. Am. Oil Chem. Soc, 1992, vol. 69, pp. 92-93.

U.S. Appl. No. 07/060,148 (Abandoned).

U.S. Appl. No. 61/243,402, filed Sep. 17, 2009 (Priority Document for WO 2011035108).

U.S. Appl. No. 61/263,695, Nov. 23, 2009 (Priority Document for WO 2011035108 and WO 2011062676).

U.S. Appl. No. 61/371,802, filed Aug. 9, 2010 (Priority Document for WO 2011062676).

U.S. Appl. No. 10/960,435 (Abandoned), filed Oct. 7, 2004.

U.S. Appl. No. 13/185,191 (Abandoned), filed Jul. 18, 2011.

U.S. Appl. No. 06/658,979 (Abandoned), filed Oct. 9, 1984.

Vertesy et al., "Frulimicins: Novel Lipopeptide Antibiotics With Peptidoglycan Synthesis Inhibiting Activity from *Actinopianes friuliensis* sp. Nov., II. Isolation and Structural Characterization" *J. of Antibiotics*, 53(8):816-27 (2000).

Woodworth et al., "Single-Dose Pharmacokinetics and Antibacterial Activity of Daptomycin, a New Lipopeptide Antibiotic, in Healthy Volunteers," Antimicrobial Agent and Chemotherapy 1992, vol. 36, pp. 318-325.

(56) References Cited

OTHER PUBLICATIONS

Woodworth et al., Tobramycin and daptomycin disposition when co-administered to healthy volunteers; Journal of Antimicrobial Chemotherapy, 1994, vol. 33 pp. 655-659.

Yakimov et al., "Characterization of a New Lipopeptide Surfactant Produced by Thermotolerant and Halotolerant Subsurface Bacillus Licheniformis BAS50," Applied and Environmental Microbiology 1995; vol. 61, pp. 1706-1713.

*Cubist Pharmaceuticals, Inc.* v. *Hospira, Inc.*, Case No. 1:12-cv-00367-GMS in the U.S. District Court for the District of Delaware, filed Mar. 21, 2012: Memorandum Opinion, dated Dec. 8, 2014 (47 pages).

Inter Partes Review of U.S. Patent No, 8,129,342, *Agila Specialties Inc. and Mylan Pharmaceuticals Inc.* v. *Cubist Pharmaceuticals, Inc.*, Case No. IPR2015-00140: [Corrected] Petition for Inter Partes Review of U.S. Pat. No. 8,129,342, dated Nov. 17, 2014 (73 pages).

Inter Partes Review of U.S. Pat. No. 8,058,238, *Agila Specialties Inc. and Mylan Pharmaceuticals Inc.*, v. *Cubist Pharmaceuticals, Inc.*, Case No. IPR2015-00141: [Corrected] Petition for Inter Partes Review of U.S. Patent No, 8,058,238; dated Nov. 17, 2014 (74 pages).

Inter Partes Review of U.S. Pat. No. 8,058,238, *Agila Specialties Inc. and Mylan Pharmaceuticals Inc.* v. *Cubist Pharmaceuticals, Inc.*, Case No. IPR2015-00142: [Corrected] Petition for Inter Partes Review of U.S. Pat. No. 8,058,238, dated Nov. 7, 2014 (69 pages).

Inter Partes Review of U.S. Pat. No. 8,058,238, *Agila Specialties Inc. and Mylan Pharmaceuticals Inc.* v. *Cubist Pharmaceuticals, Inc.*, Case No. IPR2015-00143: [Corrected] Petition for Inter Partes Review of U.S. Patent No, 8,058,238; dated Nov. 7, 2014 (73 pages).

Inter Partes Review of U.S. Pat. No. 8,058,238, *Agila Specialties Inc. and Mylan Pharmaceuticals Inc.* v. *Cubist Pharmaceuticals, Inc.*, Case No. IPR2015-00144: [Corrected] Petition for Inter Partes Review of U.S. Pat. No. 8,058,238, dated Nov. 7, 2014 (75 pages).

Brief for Defendant-Appellant Hospira, Inc. (142 pages), *Cubist Pharmaceuticals, Inc.* v. *Hospira, Inc.*, Nos. 15-1197, 15-1204 & 15-1259 (Fed. Cir. Feb. 2, 2015), ECF No. 29.

Brief for Plaintiff-Cross Appellant Cubist Pharmaceuticals, Inc. (93 pages), *Cubist Pharmaceuticals, Inc.* v. *Hospira, Inc.*, Nos. 15-1197, 15-1204 & 15-1259 (Fed. Cir. Mar. 11, 2015), ECF No. 32.

Combined Response and Reply Brief for Defendant-Appellant Hospira, Inc. (76 pages), *Cubist Pharmaceuticals, Inc.* v. *Hospira, Inc.*, Nos. 15-1197, 15-1204 & 15-1259 (Fed. Cir. Apr. 17, 2015), ECF No. 42.

Extended European Search Report issued in European Patent Application No. 15173315.8, Applicant Cubist Pharmaceuticals, Inc., including Search Opinion (12 pages).

Reply Brief for Plaintiff-Cross Appellant Cubist Pharmaceuticals, Inc. (40 pages), *Cubist Pharmaceuticals, Inc.* v. *Hospira, Inc.*, Nos. 15-1197, 15-1204 & 15-1259 (Fed. Cir. May 1, 2015), ECF No. 49.

\* cited by examiner

HIGH PURITY LIPOPEPTIDES

CROSS-REFERENCE TO RELATED APPLICATIONS

This is a continuation of U.S. patent application Ser. No. 13/918,083, filed Jun. 14, 2013, which is a continuation application of U.S. patent application Ser. No. 13/398,219, filed Feb. 16, 2012 (issued as U.S. Pat. No. 8,604,164 on Dec. 10, 2013), which is a continuation application of U.S. patent application Ser. No. 12/888,233, filed Sep. 22, 2010 (issued as U.S. Pat. No. 8,129,342 on Mar. 6, 2012), which is a continuation application of U.S. patent application Ser. No. 11/739,180, filed Apr. 24, 2007 (issued as U.S. Pat. No. 8,058,238 on Nov. 15, 2011), which is a continuation application of U.S. patent application Ser. No. 10/747,485, filed Dec. 29, 2003 (now abandoned), which is a divisional application of U.S. patent application Ser. No. 09/735,191, filed Nov. 28, 2000 (issued as U.S. Pat. No. 6,696,412 on Feb. 24, 2004), which claims the benefit of U.S. Provisional Application No. 60/177,170, filed Jan. 20, 2000, all of which are incorporated by reference herein in their entireties.

The present application contains disclosure that was the subject of a joint research agreement within the meaning of 35 U.S.C §103(c)(3), between Cubist Pharmaceuticals, Inc, and Eli Lilly and Company, and said agreement was in effect on or before the date the claimed invention was made.

TECHNICAL FIELD OF THE INVENTION

The present invention relates to a highly purified form of lipopeptides, including daptomycin, a lipopeptide antibiotic with potent bactericidal activity against gram-positive bacteria, including strains that are resistant to conventional antibiotics. The present invention also relates to a process for preparing the highly purified form of the lipopeptide. The present invention further relates to micelles of lipopeptides. The present invention also relates to pharmaceutical compositions of the lipopeptide micelles and methods of using these compositions. The present invention also relates to methods of making lipopeptide micelles from non-associated monomers of the lipopeptides, and for converting lipopeptide micelles to non-associated monomers. The present invention also relates to a process for preparing lipopeptides using micelles that is easily scaled for commercial production.

BACKGROUND OF THE INVENTION

The rapid increase in the incidence of gram-positive injections—including those caused by antibiotic resistant bacteria—has sparked renewed interest in the development of novel classes of antibiotics. One such class is the lipopeptide antibiotics, which includes daptomycin. Daptomycin has potent bactericidal activity in vitro against clinically relevant gram-positive bacteria that cause serious and life-threatening diseases. clinically relevant gram-positive bacteria that cause serious and life-threatening diseases. These bacteria include resistant pathogens, such as vancomycin-resistant enterococci (VRE), methicillin-resistant *Staphylococcus aureus* (MRSA), glycopeptide intermediary susceptible *Staphylococcus aureus* (GISA), coagulase-negative staphylococci (CNS), and penicillin-resistant *Streptococcus pneumoniae* (PRSP), for which there are very few therapeutic alternatives. See, e.g., Tally et al., 1999, *Exp. Opin. Invest. Drugs* 8: 1223-1238, hereafter "Tally". Daptomycin's inhibitory effect is a rapid, concentration-dependent bactericidal effect in vitro and in vivo, and a relatively prolonged concentration-dependent post-antibiotic effect in vivo.

Daptomycin is described by Baltz in *Biotechnology of Antibiotics, 2nd Ed.*, ed, W. R. Strohl (New York: Marcel Dekker, Inc.), 1997. pp. 415-435, hereafter "Baltz." Daptomycin, also known as LY 146032, is a cyclic lipopeptide antibiotic that can be derived from the fermentation of *Streptomyces roseosporus*. Daptomycin is a member of the factor A-21978$C_0$ type antibiotics of *S. roseosporus* and is comprised of a decanoyl side chain linked to the N-terminal tryptophan of a cyclic 13-amino acid peptide (FIG. 1). Daptomycin has an excellent profile of activity because it is highly effective against most gram-positive bacteria: it is highly bactericidal and fast-acting; it has a low resistance rate and is effective against antibiotic-resistant organisms. The compound is currently being developed in a variety of formulations to treat serious infections caused by bacteria, including, but not limited to, methicillin resistant *Staphylococcus aureus* (MRSA) and vancomycin resistant enterococci (VRE).

A number of United States Patents describe A-21978C-antibiotics and derivatives thereof including daptomycin (LY 146032) as well as methods of producing and isolating the A-21978C antibiotics and derivatives thereof.

U.S. Pat. Re. 32333, Re. 32,455 and U.S. Pat. No. 4,800,157 describe a method of synthesizing daptomycin by cultivating *Streptomyces roseosporus* NRL15998 under submerged aerobic fermentation conditions. U.S. Pat. No. 4,885,243 describes an improved method of synthesizing daptomycin by feeding a fermentation culture a decanoic fatty acid or ester or salt thereof.

U.S. Pat. Re. 32,310, Re. 32,311, U.S. Pat. Nos. 4,537,717, 4,482,487 and 4,524,135 describe methods of deacylating the A-21978C antibiotic and reacylating the peptide nucleus and antibiotic derivatives made by this process. All of these patents describe a purified deacylated A-21978C antibiotic nucleus or a derivative thereof which was isolated from the fermentation broth by filtration and then purified by Diaion HP-20 chromatography and silica gel/C18 chromatography.

U.S. Pat. Re. 32,333 and Re. 32,455 disclose a purification method in which a filtrate of whole fermentation broth was purified through a number of precipitation and extraction steps to obtain a crude A-21978C complex. The crude complex was further purified by ion exchange chromatography on IRA-68 and two rounds of silica gel chromatography. Individual A-21978C factors were separated by reverse-phase silica gel or silica gel/CIS. U.S. Pat. Re. 32,333 and Re. 32,455 also disclose that A-21978C may be purified by batch chromatography using Diaion HP-20 resin followed by silica-gel column chromatography.

U.S. Pat. No. 4,874,843 describes a daptomycin purification method in which the fermentation broth was filtered and passed through a column containing HP-20 resin. Alter elution, the semipurified daptomycin was passed through a column containing HP-20ss, and then separated again on HP-20 resin. The '843 patent, states that final resolution and separation of daptomycin from structurally similar compounds by this method is impeded by the presence of impurities that are not identifiable by ultraviolet analysis of the fermentation broth. The '843 patent further states that attempts to remove these impurities by reverse phase chromatography over silica gel, normal phase chromatography over silica gel or ion exchange chromatography also failed to significantly improve the purity of daptomycin. The '843 patent also discloses a "reverse method" for purification, comprising the steps of contacting an aqueous solution of the fermentation product with a non-functional resin in aqueous phase, physically removing the water from the charged resin, rewetting the charged resin with a polar organic solvent, washing the resin with the organic solvent, eluting the fermentation product from the resin by increasing the polarity of the solvent and recovering the fermentation product. The '843 patent teaches that this method improves the final purity from about 80% to about 93% and increases the yield from about 5% to about 35%; however, the '843 patent does not disclose the type of impurities present in the daptomycin preparation.

U.S. Pat. No. 5,912,226 describes the identification and isolation of two impurities produced during the manufacture of daptomycin. Daptomycin, an α-aspartyl peptide, becomes transpeptidated to form a stable intermediate in which the aspartyl group becomes an anhydro-succinimido group (FIG. 3). The '226 patent teaches that the presence of this intermediate, designated anhydro-daptomycin, is more pronounced at pH 4-6. Rehydration of the anhydro-succmimido form produces a second degradation product that contains an β-aspartyl group and is designated the β-isomer form of daptomycin (FIG. 2).

The '226 patent discloses that the t-BOC derivative of anhydro-daptomycin may be isolated by chromatography over reverse phase silica gel/C-18 column, precipitated, and repurified by reverse phase silica gel/C-18 chromatography. The '226 patent also teaches that the β-isomer form of daptomycin may be purified by chromatography over a Diaion HP-20ss resin, desalted by chromatography over a Diaion HP-20 resin, and further purified using a reverse-phase C-18 column followed by a HP-20 resin column in reverse mode.

Kirsch et al. (*Pharmaceutical Research*, 6:387-393, 1989, hereafter "Kirsch") stated that anhydro-daptomycin and the β-isomer were produced in the purification of daptomycin. Kirsch described methods to minimize the levels of anhydro-daptomycin and the β-isomer through manipulation of pH conditions and temperature conditions. However, Kirsch was unable to stabilize daptomycin and prevent the conversion of daptomycin to anhydro-daptomycin and its subsequent isomerization to β-isomer. Kirsch was also unable to prevent the degradation of daptomycin into other degradation products unrelated to anhydro-daptomycin and β-isomer.

The '226 patent states that daptomycin may be prepared using these procedures so that the daptomycin contains no more than 2.5% by weight of a combined total of anhydro-daptomycin and β-isomer, but gives no indication of the levels of other impurities. In the method taught in U.S. Pat. No. 4,874,843 and in large-scale preparations of daptomycin for clinical trials, the highest daptomycin purity levels observed has been about 90%-93%. There is a need for a commercially feasible method to produce more highly purified daptomycin and, if possible, to increase its yield after purification. Furthermore, it would be desirable to obtain purified daptomycin that contains little or none of anhydro-daptomycin and the β-isomer form of daptomycin. It would also be desirable to reduce the levels of a number of other impurities in daptomycin. However, there has been no method available in the art that has been shown to be able to further reduce the levels of anhydro-daptomycin, β-isomer form and other impurities in the daptomycin product.

SUMMARY OF THE INVENTION

The instant invention addresses these problems by providing commercially feasible methods to produce high levels of purified lipopeptides. In a preferred embodiment, the lipopeptide is daptomycin or a daptomycin-related lipopeptide. In one embodiment of the instant invention, commercially feasible methods are disclosed that results in daptomycin at a purity level of 95-97%. In another embodiment of the instant invention, a commercially feasible method is disclosed that almost completely eliminates the major impurities anhydro-daptomycin and β-isomer as well as other impurities in preparations of daptomycin. In another embodiment of the invention, commercially feasible methods are disclosed for purifying lipopeptides, including daptomycin or a daptomycin-related lipopeptide, comprising separating lipopeptide micelles from low molecular-weight contaminants and separating non-associated lipopeptides from high molecular weight contaminants. The invention also provides high performance liquid chromatography (HPLC) methods of analyzing the purity of daptomycin and detecting and characterizing other impurities in daptomycin, some of which were previously unknown.

The invention also provides purified daptomycin that possesses a purity of at least 98% or that is substantially or essentially free of anhydro-daptomycin and β-isomer. The invention provides purified daptomycin that, is free or essentially free of anhydro-daptomycin and contains a much lower level of β-isomer and of other contaminants than was previously possible to obtain in the prior art. The invention also provides lipopeptide micelles. In a preferred embodiment, the micelle comprises daptomycin or a daptomycin-related lipopeptide. The invention also provides pharmaceutical compositions comprising highly purified daptomycin or a daptomycin-related lipopeptide micelles and methods of using these compositions.

BRIEF DESCRIPTION OF THE DRAWINGS

FIG. 14A shows a spherical micelle, in which the hydrophobic tails of amphipathic molecules are oriented toward the center of the sphere while the hydrophilic heads of the amphipathic molecules are oriented towards the outside of the sphere, in contact with the aqueous environment. FIG. 14A shows an example in which the hydrophilic heads are negatively charged. FIG. 14B shows a lipid bilayer structure in which two layers of amphipathic molecules assemble such that the hydrophobic tails of each layer are oriented towards each other while the hydrophilic heads on either side of the bilayer are in contact with the aqueous environment. Lipid bilayers may be either spherical or planar. FIG. 14C shows a liposome, in which a lipid bilayer, such as that shown in FIG. 14B, forms a spherical structure enclosing an aqueous interior. The hydrophilic heads of the liposome face the aqueous interior and the external aqueous environment.

DETAILED DESCRIPTION OF THE INVENTION

Objects of the Invention

Figure 1:
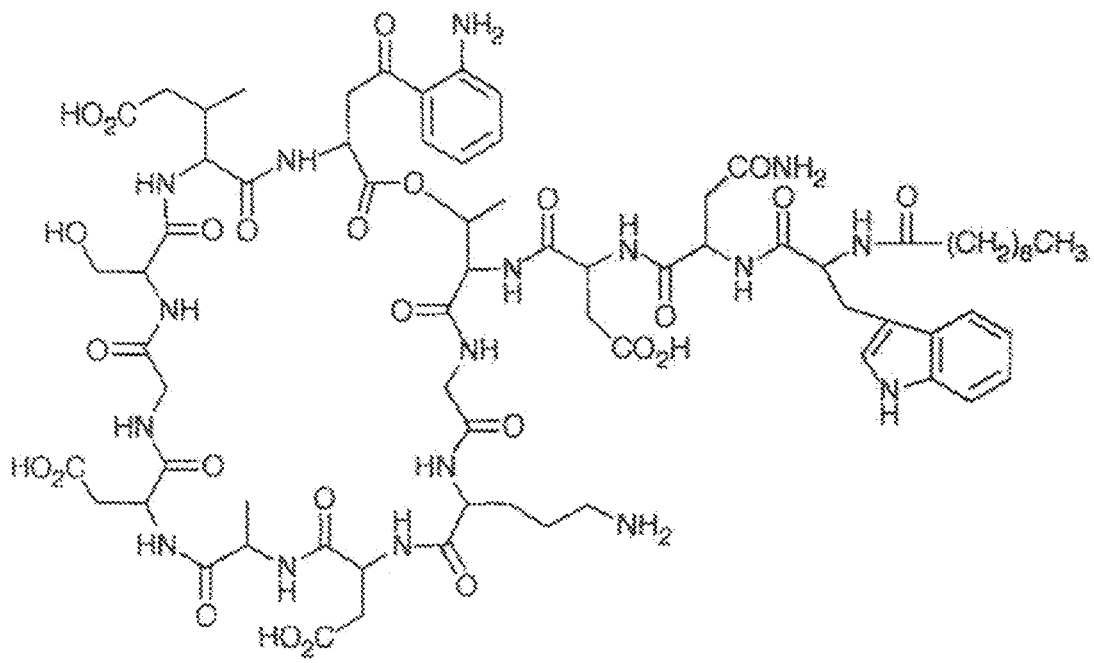
FIG. 1 shows the structure of daptomycin.

One object of the present invention is to provide a method for purifying lipopeptides that is easily scaled for commercial production comprising a unique combination of anion exchange chromatography and hydrophobic interaction chromatography. In a preferred embodiment, the method is used to manufacture purified daptomycin that is greater than 95% pure and exhibits reduced levels of impurities compared to daptomycin prepared by prior art methods. In another preferred embodiment, the method is used to manufacture daptomycin using reduced levels of solvents compared to those used in prior art methods. In another preferred embodiment, the method is used to manufacture purified daptomycin-related lipopeptides that are greater than 95% pure.

Another object of the present invention is to provide a method for increasing the levels of a lipopeptide produced by a microorganism by feeding the fermentation culture a reduced level of a fatty acid. Using lower levels of decanoic acid than those proposed for daptomycin fermentation in U.S. Pat. No. 4,885,243 results in improved economies in addition to producing a highly pure form of daptomycin or a daptomycin-related lipopeptide. In a preferred embodiment, the method is used to increase the concentration and amount of daptomycin produced by *Streptomyces roseosporus* while minimizing the production of related contaminants. Lower levels of contaminants in the fermentation broth results in a more efficient recovery and purification of daptomycin, which provides for a manufacturing process with a higher yield.

Another object of the present invention is to provide a method for purifying daptomycin or daptomycin related lipopeptides comprising the use of modified buffer enhanced anion exchange chromatography. In a preferred embodiment, the method is used to produce daptomycin that is at least 98% pure or that is substantially or essentially free of anhydrodaptomycin or β-isomer. In another preferred embodiment, the method is used to purity daptomycin-related lipopeptides to at least 98% purity.

Another object of the present invention is to provide a process chromatography method to purify a lipopeptide comprising a novel combination of anion exchange chromatography, hydrophobic interaction chromatography and modified buffer enhanced anion exchange chromatography. In a preferred embodiment, the process chromatography method is used to purify daptomycin or a daptomycin-related lipopeptide. The modified buffer unexpectedly permits a separation of anhydro-daptomycin from daptomycin not previously possible in prior chromatography methods.

Another object of the invention is to provide a method for purifying lipopeptides that is easily scaled for commercial production using lipopeptide micelles. In one embodiment, the method comprises converting a lipopeptide solution from a monomeric, nonmicellar state to a micellar state and back again during purification procedures. In a preferred embodiment, the method comprises subjecting the lipopeptides to conditions in which micelles are formed, separating the lipopeptide micelles from low molecular weight contaminants by, e.g., a size separation technique. In another preferred embodiment, the method comprises subjecting the lipopeptides to conditions in which the lipopeptides are in monomeric form and separating the monomeric lipopeptide molecules from high molecular weight molecules or aggregates by, e.g., a size separation technique. In a more preferred embodiment the method comprises both steps: subjecting the lipopeptides to conditions in which micelles are formed and separating the lipopeptide micelles from low molecular weight contaminants, and then subjecting the lipopeptide micelles to conditions in which the lipopeptides are in monomeric form and separating the lipopeptide monomers from high molecular weight molecules or aggregates. These two steps may be performed in either order. In an even more preferred embodiment, the size separation technique is ultrafiltration or size exclusion chromatograph.

A further object of the present invention is to provide improved methods for measuring the purity of lipopeptides, including daptomycin, by high pressure liquid chromatography (HPLC).

Another object of the present invention is to provide purified lipopeptides, such as daptomycin or a daptomycin-related lipopeptide, and pharmaceutically acceptable salts or formulations thereof. In a preferred embodiment, the present invention provides daptomycin or a daptomycin-related lipopeptide purified by one of the methods described in the specification. The present invention also provides pharmaceutical compositions of a purified lipopeptide or its salts and methods of administering these compositions. In a preferred embodiment, the pharmaceutical composition comprises purified daptomycin.

Another object of the present invention is to provide lipopeptide micelles and pharmaceutically acceptable formulations thereof. In a preferred embodiment, the present invention provides daptomycin micelles or a daptomycin-related lipopeptide micelle and pharmaceutically acceptable formulations thereof. In another embodiment, the invention also provides methods of administering the lipopeptide micelles or pharmaceutical formulations thereof to patients in need thereof. In a preferred embodiment, the lipopeptide micelles are administered intravenously, parenterally, intramuscularly or topically.

DEFINITIONS

Unless otherwise defined, all technical and scientific terms used herein have the meaning as commonly understood by one of ordinary skill in the art to which this invention belongs. The practice of the present invention employs, unless otherwise indicated, conventional techniques of chemistry, biochemistry and microbiology and basic terminology used therein.

The term "isolated" refers to a compound or product that is refers to a compound which represents at least 10%, preferably at least 20% or 30%, more preferably at least 50%, 60% or 70%, and most preferably at least 80% or 90% of the compound present in the mixture.

The term "lipopeptide" refers to a molecule that comprises a lipid-like moiety covalently linked to a peptide moiety, as well as salts, esters, amides and ethers thereof. The term "lipopeptide" also encompasses protected forms of lipopeptides in which one or more amino, carboxylate or hydroxyl groups are protected. See, e.g., "Protective Groups in Organic Synthesis" by Theodora W. Greene, John Wiley and Sons, New York, 1981 for examples of protecting groups. In a preferred embodiment, the lipopeptide is an antibiotic. In another preferred embodiment, the lipopeptide is LY 303366, echinocandins, pneumocandins, aculeacins, surfactin, plipastatin B1, amphomycin or the lipopeptide derivative disclosed in U.S. Pat. No. 5,629,288. These lipopeptides are known in the art. See, e.g., U.S. Pat. No. 5,202,309 and International PCT Application WO 00/08197. In another preferred embodiment, the lipopeptide is a daptomycin-related molecule, including, inter alia, daptomycin, A54145, a daptomycin-related lipopeptide disclosed in U.S. Pat. Nos. 4,537,717, 4,482,487, Re. 32,311, Re. 32,310, 5,912,226, currently in reissue as U.S. Ser. No. 09/547,357, U.S. Provisional Applications Nos. 60/170,943, 60/170,946 or 60/170,945, filed Dec. 15, 1999, U.S. Provisional Application No. 60/208,222, filed May 30, 2000, all of which are specifically incorporated herein by reference, or an A-21978 antibiotic in which the n-decanoyl fatty acid side chain of daptomycin is replaced by an n-octanoyl, n-nonanoyl, n-undecanoyl, n-dodecanoyl, n-tridecanoyl or n-tetradecanoyl fatty acid side chain. The daptomycin-related lipopeptides disclosed in 60/170,943, 60/170,946, 60/170,945, and 60/208,222 relate to synthetic and semisynthetic lipopeptides in which the ornithine or kynurine residues or the fatty acid side chain of daptomycin are modified. In a more preferred embodiment, the lipopeptide is daptomycin. The term daptomycin-related lipopeptide refers to compounds described above, and salts thereof.

The term "daptomycin" refers to the n-decanoyl derivative of the factor A-21978$C_0$ type antibiotic, or a pharmaceutical acceptable salt thereof. "Daptomycin" is synonymous with LY146032. See FIG. 1.

Figure 3:
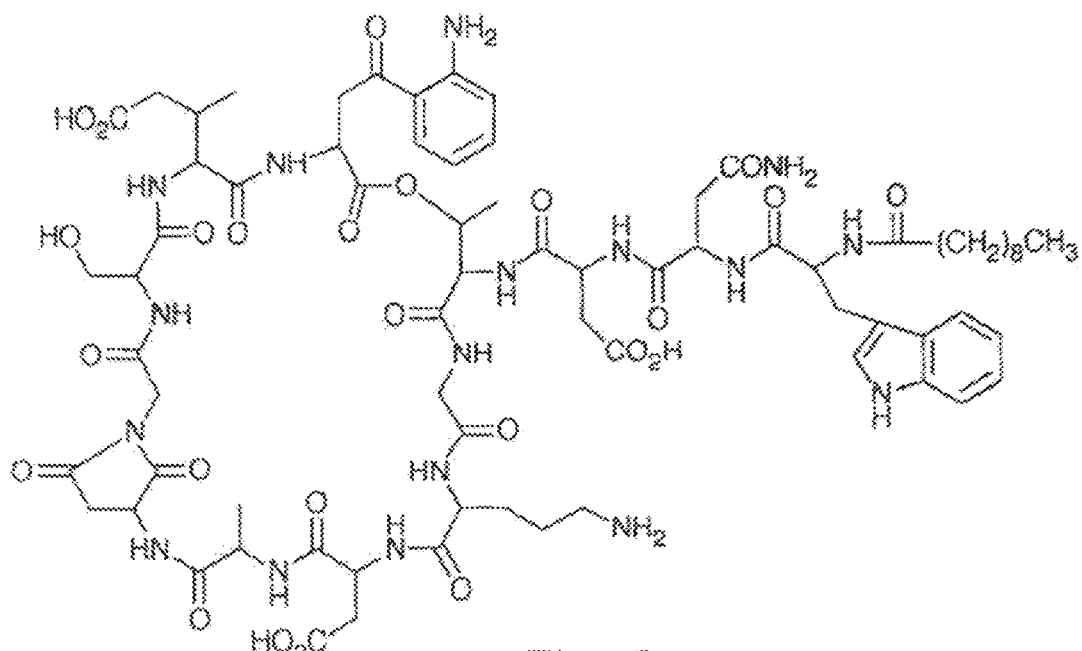
FIG. 3 shows the structure of impurity 13, CB-130952 (previously identified as anhydro-daptomycin, LY178480).

The term "anhydro-daptomycin" refers to the daptomycin derivative in which the α-aspartyl group of daptomycin is transpeptidated to an anhydro-succmimido group. See FIG. 3.

The term "β-isomer" or "β-isomer of daptomycin" refers to the daptomycin derivative that contains a β-aspartyl group instead of an α-aspartyl group. See FIG. 2.

Daptomycin or a daptomycin-related lipopeptide is "substantially pure" when at least 95% of a sample is daptomycin or daptomycin-related lipopeptide. Preferably, daptomycin or daptomycin-related lipopeptide is "substantially pure" when at least 97% of a sample is daptomycin or daptomycin-related lipopeptide.

Daptomycin or daptomycin-related lipopeptide is "essentially pure" when at least 98% of a sample is daptomycin or daptomycin-related lipopeptide. Preferably, daptomycin or daptomycin-related lipopeptide is "essentially pure" when at least 99% of a sample is daptomycin or daptomycin-related lipopeptide.

Daptomycin or daptomycin-related lipopeptide is "substantially free" of another compound when the other compound is present in an amount that is no more than 1% of the amount of the daptomycin or daptomycin-related lipopeptide preparation.

Daptomycin or daptomycin-related lipopeptide is "essentially free" of another compound when the other compound is present in an amount that is no more than 0.5% of the amount of the daptomycin or daptomycin-related lipopeptide preparation.

Daptomycin or daptomycin-related lipopeptide is "free" of another compound when the other compound is present in an amount that is no more than 0.1% of the amount of the daptomycin or daptomycin-related lipopeptide preparation. Alternatively, daptomycin or daptomycin-related lipopeptide is "free" of another compound when the compound cannot be detected by HPLC under conditions of maximum sensitivity in which a limit of detection is approximately 0.05% or less of the amount of the daptomycin or daptomycin-related lipopeptide preparation. Exemplary HPLC methods are described herein (Tables 1 and 2).

"Purified" daptomycin or daptomycin-related lipopeptide refers to substantially pure daptomycin or daptomycin-related lipopeptide, essentially pure daptomycin or daptomycin-related lipopeptide, or a salt thereof, or to daptomycin, daptomycin-related lipopeptide, or a salt-thereof which is substantially free, essentially free, or free of another compound.

"Partially purified" daptomycin or daptomycin-related lipopeptide refers to daptomycin, daptomycin-related lipopeptide, or a salt thereof that is less than 90% pure.

The purity of daptomycin, daptomycin-related lipopeptide or of another lipopeptide refers to the lipopeptide prior to its formulation in a pharmaceutical composition. The purity may be measured by any means including nuclear magnetic resonance (NMR), gas chromatography/mass spectroscopy (GC/MS), liquid chromatography/mass spectroscopy (LC/MS) or microbiological assays. A preferred means for measuring the purity of daptomycin is by analytical high pressure liquid chromatography (HPLC).

Figure 14A:
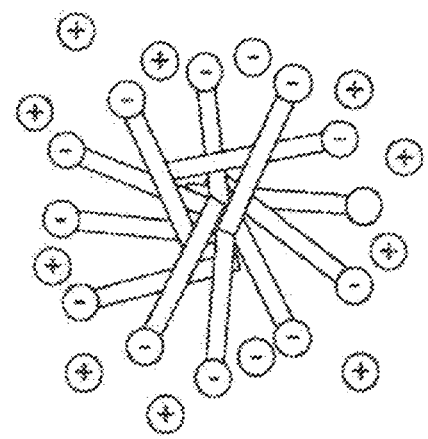
FIGS. 14A-14C show micellar structures.
Figure 14B:
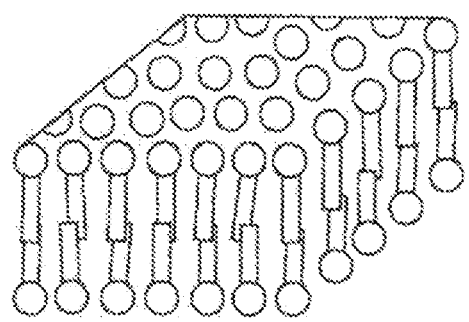
Figure 14C:
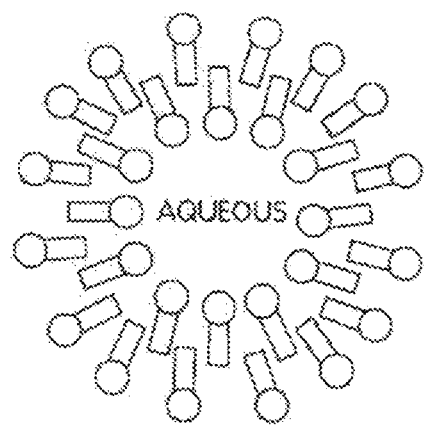

The term "micelle" refers to aggregates of amphipathic molecules. In an aqueous media, the lipophilic domains of the molecules of the aggregate are oriented toward the interior of the micelle and the hydrophilic domains are in contact with the medium. Micelle structures include, but are not limited to, spherical, laminar, cylindrical, ellipsoidal, vesicular (liposomal), lamellar and liquid crystal. See FIG. 14.

The term "mixed micelle" refers to a particular type of micelle in which the micelle contains more than a single type of amphipathic molecule. In the context of this invention, mixed micelles contain a lipopeptide and at least one other amphipathic molecule which may be another lipopeptide. Mixed micelles contain at least 10% of the lipopeptide by weight. In other embodiments, a mixed micelle contains at least 20%, 30%, 40%, 50%, 60%, 70%, 80% or 90% of the lipopeptide.

The term "micellar solution" refers to a solution in which more than 50% of the lipopeptide molecules in the solution are present in micelles, as measured by weight. Preferably, at least 60%, 70%, 80%, 90% or 95% of the molecules are present in micelles. A micellar solution is retained on a ultrafiltration, membrane that has a 10,000 dalton nominal molecular weight (NMW) cutoff.

The term "critical micelle concentration" (cmc) refers to the particular concentration of molecules, which is dependent upon temperature, salt concentration and the nature and type of amphipathic molecule. Above the cmc, the unassociated monomers and micelles exist in equilibrium.

The term "monomer" refers to an amphipathic molecule that is not part of an aggregate but that exists as a single molecule. In the context of this invention, the term monomer refers to a non-associated lipopeptide.

The term "monomeric solution" refers to a solution in which more than 50% of the lipopeptide molecules are present as monomers as measured by weight. Preferably at least 60%, 70%, 80%, 90% or 95% are present as monomers. A monomeric solution is not retained on a ultrafiltration membrane that has a 10,000 dalton NMW cutoff but rather passes through the membrane.

The term "low ionic strength buffer" refers to a solution that has a salt concentration below 50 mM; the term "medium tonic strength buffer" refers to a solution that has a salt concentration between 50-250 mM; the term "high ionic strength buffer" refers to a solution that has a salt concentration greater than 250 mM.

Methods for Manufacturing Purified Lipopeptides

One embodiment of the present invention is drawn to a process chromatography method that produces a purified lipopeptide in a commercially feasible manner. In a preferred embodiment, the lipopeptide is daptomycin or a daptomycin-related lipopeptide. The process chromatography method comprises sequentially using anion exchange chromatography, hydrophobic interaction chromatography (HIC) and anion exchange chromatography to purify a preparation containing a lipopeptide, such as daptomycin or a daptomycin-related lipopeptide.

In a preferred embodiment of the instant invention, the purification method further comprises altering the fermentation conditions in which the A21978C-containing crude product is produced by *Streptomyces roseosporus* in order to increase daptomycin production and decrease impurities and related contaminants produced by the *S. roseosporus* fermentation culture.

A preferred embodiment of the process chromatography method is described below:

*Streptomyces roseosporus* is fermented with a feed of n-decanoic acid, as disclosed in U.S. Pat. No. 4,885,243, with the modification that the decanoic acid feed is kept at the lowest levels possible without diminishing the overall yield of the fermentation. In a preferred embodiment, the residual decanoic acid is maintained at less than 50 parts per million (ppm) during aerobic fermentation. In a more preferred embodiment, the residual decanoic acid is maintained between one and 20 ppm during aerobic fermentation. In an even more preferred embodiment, the residual decanoic acid is maintained at approximately ten ppm during aerobic fermentation. In a preferred embodiment, the concentration of residual decanoic acid is measured throughout fermentation and the feed level of decanoic acid is adjusted to continuously keep the residual decanoic acid levels within the preferred parameters. The prior art does not describe the in situ specific and low residual constant decanoic acid concentrations required to achieve optimal expression of daptomycin containing lower levels of impurities.

After fermentation, the extracellular solution is clarified by removing the mycelia from the fermentation broth. Removing the mycelia from the fermentation is performed by any standard separation technique, such as centrifugation or microfiltration. In a preferred embodiment, the fermentation broth is clarified by microfiltration, such as by using a Pall Sep™ membrane system. In a more preferred embodiment, the fermentation broth is clarified using an industrial centrifuge, such as a Westfalia™ centrifuge, followed by a finishing depth filter. Other devices, such as filter presses, rotary drum filters or disposable depth filters, may be used to remove mycelia from fermentation broth to produce a clarified broth suitable for large-scale column chromatography.

In another embodiment, daptomycin may be extracted from mycelial fermentation directly by using an organic solvent such as butanol prior to clarification on a solvent separating centrifuge or filter. Any alcohol with four carbons or more may be used in the extraction according to this embodiment. A preferred solvent is n-butanol. Using an organic solvent results in an initial additional purification of daptomycin compared to a purely aqueous separation of daptomycin. For example, daptomycin partitions into n-butanol when n-butanol is used in a concentration greater than 10% and when the process is conducted under conditions in which the n-butanol forms a separate phase, e.g., at a pH value of 4-5, which is near the isoelectric point of daptomycin (see Example 4).

In another embodiment, daptomycin is produced in an immobilized reactor that uses preactivated mycelia for the non-fermentation production of daptomycin using an energy source, preferably a sugar, elemental components, such as amino acids and ammonia, and decanoic acid. Production of daptomycin in an immobilized enzyme reactor is then processed by methods described herein.

After clarification of the fermentation broth, the levels of daptomycin are enriched, (i.e. concentrated) in the clarified solution by anion exchange chromatography. The clarified solution is first contacted with an anion exchange resin under conditions in which most or all of daptomycin binds to the anion exchange resin. After binding, the resin is washed with an appropriate ionic aqueous buffer to remove unbound material and some of the daptomycin impurities. Finally, the purified daptomycin bound to the resin is eluted under conditions in which daptomycin will dissociate from the resin.

The binding, washing and elution steps may be performed according to this invention using buffers and methods known in the art. For instance, elution may be performed by using a buffer containing an elevated salt concentration compared to the wash buffer, a buffer that has a lower pH compared to the wash buffer, or a buffer that has both a higher salt concentration and a lower pH than the wash buffer. In a preferred embodiment, daptomycin is bound to the anion exchange resin that has been equilibrated in a buffer containing no added salt or a low salt concentration at a pH that is neutral to basic. The loaded resin is washed with three column bed volumes of water and then three to six bed volumes of an intermediate salt buffer containing 30 to 60 mM NaCl. Daptomycin is eluted from the column with one to three column volumes of an elevated salt and/or lower pH buffer containing 300 to 500 mM NaCl. Higher concentrations of sodium chloride and alternative salts such as potassium chloride will also elute daptomycin from the resin. In a preferred embodiment, a high flow rate anionic exchange resin is used. In a more preferred embodiment, FP-DA 13 resin (Mitsubishi) is used.

The anion exchange chromatography may be performed by column chromatography or may be accomplished in batch mode. For commercial production, it may be preferred to use batch mode. The anion exchange resin may be washed and eluted with stepwise salt gradients or with a continuous salt gradient. A suitable stepwise or continuous salt gradient is any one that permits the separation of daptomycin from contaminants. In a preferred embodiment, a continuous salt gradient is one which ranges from 0 to 1000 mM NaCl. In a more preferred embodiment, a continuous salt gradient is one which ranges from 100 to 500 mM NaCl or from 0 to 400 mM NaCl. Radial flow chromatography may also be used, as described in U.S. Pat. Nos. 5,756,680, 4,865,729, 4,840,730 or 4,708,782.

After anion exchange chromatography, the daptomycin preparation is further purified by hydrophobic interaction chromatography (HIC). One embodiment of this step is described in U.S. Pat. No. 4,874,843, herein incorporated by reference. The eluted aqueous daptomycin preparation is contacted with a HIC resin under conditions in which most or all of daptomycin will bind to the resin. The water content of the daptomycin-loaded resin is reduced by contacting the resin with an increased concentration of a non-polar solvent. The resin is washed with an appropriate polar organic solvent under conditions in which impurities dissociate from the resin while daptomycin remains bound. Finally, the daptomycin preparation is eluted under conditions in which daptomycin dissociates from the resin. In general, daptomycin is eluted using a solvent-containing buffer with a lower polarity (higher polar solvent level) and/or higher pH than the wash buffer.

In a preferred embodiment, the non-functional resin for HIC is small particle HP-20ss (Mitsubishi). The bound daptomycin is specifically removed from the HP-20ss resin with ah organic phase solvent, such as one containing isopropyl alcohol, acetonitrile, butanol or other suitable solvent. In a more preferred embodiment, daptomycin is bound to HP-20ss resin that has been equilibrated in an acetate buffer containing 10% acetonitrile or equivalent polar solvent, such as isopropyl alcohol. The daptomycin-loaded resin is washed with at least three column bed volumes of equilibration buffer. The daptomycin-loaded resin is further freed of additional impurities by washing with three to six bed volumes of an acetate wash buffer containing a non-eluting concentration of the polar solvent. In a preferred embodiment, the daptomycin-loaded resin is washed with 30% acetonitrile or 45% isopropyl alcohol. The daptomycin-loaded resin is eluted with one to three bed volumes of acetate buffer containing 35% or more acetonitrile or greater than 50% isopropyl alcohol. In a preferred embodiment, daptomycin is eluted with 35% acetonitrile at pH 4.0-5.0 or 55-60% isopropyl alcohol. In another embodiment, the daptomycin-loaded resin is eluted with one to three bed volumes of buffer at an increased pH. In this embodiment, the pH of the buffer is gradually increased to elute different compounds from the column at different rates due to charge differences. At elevated pH, e.g., pH 6.0-7.0, the elation concentration of acetonitrile is reduced to 10-20%. Similarly, at elevated pH, e.g., pH 6.0-7.0 the elution concentration of isopropyl alcohol is reduced to 20-25%. Control of the temperature under which chromatography is performed also influences solvent concentration. Elution at lower temperatures, i.e., under refrigerated conditions, requires increased levels of solvent at all pH conditions.

After HIC, the organic solvent in the daptomycin preparation is reduced by anion exchange chromatography. In a preferred embodiment, FP-DA 13 is used as discussed supra.

After the second anion exchange chromatography, the purified daptomycin is depyrogenated, filtered and concentrated under refrigerated conditions. Filtering daptomycin may be performed by any method known in the art. In one embodiment, filtering and depyrogenating may be performed by:

i) providing a daptomycin solution under conditions in which the daptomycin is in a monomeric and nonmicellar state;

ii) filtering the daptomycin solution under conditions in which the daptomycin will pass through the filter but pyrogens will not pass through the filter, e.g., having the daptomycin solution at pH 6.0-8.0 and filtering the solution with an ultrafilter that is rated between 3,000 NMW and 30,000 NMW;

iii) altering the daptomycin solution that has passed through the filter such that the daptomycin aggregates, e.g., by changing the pH of the daptomycin solution to 2.5-4.5 such that daptomycin forms micelles;

iv) filtering the daptomycin solution under conditions in which the daptomycin will be retained on the filter, e.g., concentrating the daptomycin on an ultrafilter of 30,000 NMW or less, such as a reverse osmosis membrane; and v) collecting the depyrogenated daptomycin.

In a preferred embodiment, daptomycin of step (ii) is filtered under pressure on a 10,000 dalton molecular weight cutoff (MWCO) ultra-filter at a pH of approximately 7-8. In a more preferred embodiment, daptomycin is at an initial concentration of less than 40 mg/ml, more preferably, at a concentration of approximately 31.25 mg/mL. Under these conditions, daptomycin passes through the filter but pyrogens such as lipopolysaccharides (LPS) do not. After the initial ultra-filtration, the pH of the filtrate is lowered to pH 2.5 to 4.5 and the filtrate is concentrated on a 10,000 MWCO ultra-filter to approximately 120 mg/mL. Under these conditions, daptomycin is retained on the filter. In a preferred embodiment, the pH of the filtrate is pH 3.5. Subsequent to concentration, the concentration of daptomycin is adjusted to 105 mg/mL, checked for endotoxin levels, and used to fill vials under aseptic conditions.

In another embodiment, reverse osmosis nanofiltration is performed at pH 1.5-3.0. The low pH and refrigerated conditions are used to retard degradation of purified daptomycin. Daptomycin may be further filtered through a 0.2 µm filter to reduce bioburden and then lyophilized either in bulk or in vials.

As an alternative to the above ultra-filtration and concentration step, the eluted fractions containing daptomycin are mixed with butanol (either n-, iso- or t-butanol) at a pH of approximately 4.5, in a ratio of greater than one part butanol to nine parts daptomycin solution. In a preferred embodiment, one part butanol is mixed with four parts daptomycin solution to yield a 20% butanol solution. The butanol-daptomycin solution is allowed to separate into organic and aqueous phases. Daptomycin partitions into the organic phase, which is collected. The dehydration of daptomycin in the organic solvent may stabilize daptomycin and prevent the degradation of the purified daptomycin to anhydro-daptomycin and subsequent formation of β-isomer. Finally, daptomycin can be returned to the aqueous phase by adding buffer at pH 6.5-7.5 to the organic phase. After concentration or collection of daptomycin, daptomycin is lyophilized.

In another embodiment of the instant invention, the process chromatography method is used to purify lipopeptides other than daptomycin, such as A54145, LY303366, echinocandins, pneumocandins, aculeacin, surfactin, plipastatin B1, amphomycin or the lipopeptide derivative disclosed in U.S. Pat. No. 5,629,288. In another embodiment, the process chromatography method is used to purify daptomycin-related lipopeptides, including A54145, or a lipopeptide disclosed in U.S. Pat. Nos. 4,537,717, 4,482,487, Re. 32,311, Re. 32,310, 5,912,226, currently in reissue as U.S. Ser. No. 09/547,357, U.S. Provisional Applications Nos. 60/170,943, 60/170,946 or 60/170,945, filed Dec. 15, 1999, U.S. Provisional Application No. 60/208,222, filed May 30, 2000, or an A-21978 antibiotic in which the n-decanoyl fatty acid side chain of daptomycin is replaced by an n-octanoyl, n-nonanoyl, n-undecanoyl, -dodecanoyl, n-tridecanoyl or n-tetradecanoyl fatty acid side chain.

In another embodiment of the instant invention, a "Salt Cloud Method" [*Genetic Engineering News*, Vol. 19, No. 20, pages 1, 34 and 43, (Nov. 15, 1999)] is used in the purification of daptomycin or other lipopeptides. The Salt Cloud Method is a membrane-based system that combines selective separations with high-volume throughput. The Salt Cloud Method can be used in conjunction with those process steps disclosed herein or separately to purify daptomycin or other lipopeptides.

Another embodiment of the instant invention is drawn to a chromatography method that produces a highly purified lipopeptide not achievable by prior art chromatography methods. The chromatography method comprises the use of modified buffer enhanced anion exchange chromatography to purify a preparation containing a lipopeptide. In a preferred embodiment, the method is used to produce highly purified daptomycin or a daptomycin-related lipopeptide. This method, when used with partially purified daptomycin, produces daptomycin that is at least 98% pure. The method also produces daptomycin that is free or essentially free of anhydro-daptomycin. The method comprises the following steps:

Partially purified daptomycin is prepared by any method known in the art or as described herein. The daptomycin preparation is then further purified by modified buffer enhanced anion exchange chromatography. Daptomycin is bound to anion exchange resin in the presence of an appropriate ionic modified buffer under conditions in which daptomycin binds to the resin ion in a monomeric and non-micellar state. The modified buffer comprises a buffering agent, such as, without limitation, acetate, phosphate, citrate and Tris-HCl, or any other buffering agent that buffers well at neutral pH. The modified buffer further comprises one or more chaotropic agents, including, without limitation, guanidine, ammonia, urea, a strong reducing agent, benzoate, ascorbate or another ionic enhancer capable of modifying the buffer so that daptomycin is easily separated from impurities. The daptomycin-loaded resin is washed with an appropriate ionic modified buffer to elute impurities, including anhydro-daptomycin. Daptomycin is then eluted under conditions that permit the separation of daptomycin from impurities that remain bound to the resin, including the β-isomer.

In a preferred embodiment, the modified buffer is at a neutral pH (a pH of 6 to 8) and contains 2 to 6 M urea. In a further preferred embodiment, the anion exchange resin is Porous Resin P150 or Porous D50 (PE Biosystems). In a more preferred embodiment, the anion exchange resin is Porous P150. In a preferred embodiment, daptomycin is bound to the resin in a low ionic strength buffer, washed with a low to medium ionic strength buffer and eluted with a high ionic strength buffer. In one preferred embodiment, daptomycin is bound to the Porous P150 resin in a Tris buffer pH 7.0 containing 6 M urea. The daptomycin-loaded Porous P150 resin is washed with three bed volumes of Tris buffer or other suitable buffer containing a salt level that removes contaminants and anhydro-daptomycin without eluting daptomycin. Daptomycin is eluted from the Porous P150 resin with Tris buffer or other suitable buffer under elevated salt conditions that will leave additional impurities, including a significant portion of β-isomer, bound to the column. In another preferred embodiment, Poros P150 is used and daptomycin is bound to the resin in an acetate buffer pH 6.0 containing 2 M urea. The daptomycin-loaded Poros P150 resin is washed and eluted similar to the method above except that an acetate buffer pH 6.0 containing 2 M urea is used. Product fractionation may be measured by HPLC or by UV monitoring.

The modified buffer enhanced anion exchange chromatography may be performed by column chromatography or may be accomplished in batch mode. Radial flow chromatography may also be used, as described in U.S. Pat. Nos. 5,756,680, 4,865,729, 4,840,730 or 4,708,782. The modified buffer enhanced anion exchange resin may be washed and eluted with stepwise salt gradients or with a continuous salt gradient. A suitable stepwise or continuous salt gradient is any one that permits the separation of daptomycin from impurities including, but not limited to, anhydro-daptomycin and β-isomer. In a preferred embodiment, a continuous salt gradient is 0 to 1000 nM NaCl. In a more preferred embodiment, the salt gradient is 100 to 500 mM NaCl or 0 to 400 mM NaCl.

In another embodiment of the instant invention, modified buffer enhanced anion exchange chromatography is used to purify lipopeptide compounds other than daptomycin. These lipopeptide compounds include, without limitation, A54145, LY303366, echinocandins, pneumocandins, aculeacin, surfactin and plipastatin B1 (Tsuge et al., 1996, Arch. Microbiol. 165:243-51) and lipopeptide derivatives as shown in U.S. Pat. No. 5,629,288. In another embodiment, modified buffer enhanced anion exchange chromatography is used to purify a daptomycin-related lipopeptide such as A54145, or a lipopeptide disclosed in U.S. Pat. Nos. 4,537,717, 4,482,487, Re. 32,311, Re. 32310, 5,912,226, currently in reissue as U.S. Ser. No. 09/547,357, U.S. Provisional Applications Nos. 60/170,943, 60/170,946 or 60/170,945, filed Dec. 15, 1999, U.S. Provisional Application No. 60/208,222, filed May 30, 2000, or an A-21978 antibiotic in which the n-decanoyl fatty acid side chain of daptomycin is replaced by an n-octanoyl, n-nonanoyl, n-undecanoyl, -dodecanoyl, n-tridecanoyl or n-tetradecanoyl fatty acid side chain.

In another embodiment of the instant invention, a novel combination of process chromatography steps is used to purify daptomycin or a daptomycin-related lipopeptide. The method comprises anion exchange chromatography, small particle reverse phase chromatography and modified buffer enhanced anion exchange chromatography. The purification method may further comprise altering the fermentation conditions in which the A21978C-containing crude product is produced by Streptomyces roseosporus. These methods produce daptomycin or a daptomycin-related lipopeptide that is at least 98% pure. In a preferred embodiment, the methods produce daptomycin or a daptomycin-related lipopeptide that is more than 99% pure.

A preferred embodiment of the process chromatography method is described below:

Streptomyces roseosporus is fermented with a feed of n-decanoic acid, as disclosed in U.S. Pat. No. 4,885,243, with the modification that the decanoic acid feed is kept at the lowest levels possible without diminishing the overall yield of the fermentation as described supra. In an alternative embodiment, a different feedstock may be used so long as it ultimately provides an n-decanoyl group for addition to the daptomycin nucleus. Examples of these feedstocks are, without limitation, decanoic amide, decanoic esters including butyl esters, crude sources of coconut or palm oil, animal source decanoic acid, various salts of decanoic acid, and petrochemical sources of decanoic acid. After fermentation, the extracellular solution is clarified as described supra. In an alternative embodiment, daptomycin may be extracted from mycelia using an organic solvent such as n-butanol prior to clarification on a solvent separating centrifuge or filter as described supra. After clarification of the fermentation broth, the level of daptomycin is enriched in the clarified solution first by anion exchange chromatography and then by HIC as described supra.

After completion of HIC, the organic solvent in the daptomycin preparation is reduced by any method known in the art. In a preferred embodiment, the organic solvent is reduced by anion exchange chromatography, as described supra. Daptomycin should be eluted from the column in a buffer compatible with the buffer required for the modified buffer enhanced chromatography. Alternatively, the elution buffer may be exchanged for the modified buffer by reverse osmosis or filtration on a 10,000 MWCO filter. In another preferred embodiment, the organic solvent is reduced by evaporation or dilution in buffer. In a third preferred embodiment, the reverse phase chromatography solvent and residual salt is removed using reverse osmosis at pH 1.5-4.0 or ultrafiltration at pH 2.5-4.5. The resultant product may be frozen for bulk storage or dried by lyophilization and then rehydrated in water or in the buffer used for the modified buffer enhanced anion exchange chromatography.

Daptomycin is further purified by modified buffer enhanced anion exchange chromatography as described supra.

After modified buffer enhanced anion exchange chromatography, the purified daptomycin is filtered and concentrated under refrigerated conditions. Filtering daptomycin may be performed by any method known in the art. In a preferred embodiment, daptomycin is depyrogenated and concentrated as described supra. Alternatively, daptomycin may be concentrated by reverse osmosis under refrigerated conditions at a pH of 1.5 to 4. The low pH and refrigerated conditions are used to retard the degradation of purified daptomycin.

As an alternative or in addition to the above filtration and concentration step, the eluted fractions containing daptomycin from the modified buffer enhanced anion exchange chromatography may be mixed with butanol (either n-, iso- or t-butanol) at a pH of approximately 4.5, in a ratio of greater than one part butanol to nine parts daptomycin solution. In a preferred embodiment, one part butanol is mixed with four parts daptomycin solution to yield a 20% butanol solution. The butanol-daptomycin solution is allowed to separate into organic and aqueous phases. Daptomycin partitions into the organic phase, which is collected. The dehydration of daptomycin in the organic solvent may stabilize daptomycin and prevent the degradation of the purified daptomycin to anhydro-daptomycin and subsequent formation of β-isomer.

After concentration or collection, of daptomycin, daptomycin is lyophilized.

In another embodiment of the instant invention, the process chromatography is used to purify lipopeptides other than daptomycin, such as those described supra.

Formation of Lipopeptide Micelles and Methods of Use Thereof

Another embodiment of the invention provides lipopeptide micelles, methods for forming lipopeptide micelles and methods of using the lipopeptide micelles for lipopeptide purification and pharmaceutical compositions. In a preferred embodiment, the lipopeptide is a daptomycin-related molecule, including, inter alia, daptomycin, A54145, a daptomycin-related lipopeptide disclosed in U.S. Pat. Nos. 4,537,717, 4,482,487, Re. 32,311, Re. 32,310, 5,912,226, currently in reissue as U.S. Ser. No. 09/547,357, U.S. Provisional Applications Nos. 60/170,943, 60/170,946 or 60/170,945, filed Dec. 15, 1999, U.S. Provisional Application No. 60/208,222, filed May 30, 2000, or an A-21978 antibiotic in which the n-decanoyl side chain of daptomycin is replaced by an n-octanoyl, n-nonanoyl, n-undecanoyl, n-dodecanoyl, -tridecanoyl or n-tetradecanoyl side chain. In a more preferred embodiment, the lipopeptide is daptomycin.

Micelles are aggregates of amphipathic molecules. In aqueous media, the lipophilic parts of the molecules are oriented toward the interior of the micelle and the hydrophilic parts of the molecules are in contact with the aqueous media. Micelles form spontaneously in a solution containing amphipathic molecules if the concentration of the molecules is high enough.

Micelle formation causes changes in several bulk physical properties of a solution including changes in osmotic pressure, turbidity, electrical conductance, surface tension, co-ion and counterion activities (in the case of ionic, amphipathic molecules), refractive index, UV and NMR spectra, partial molar volume, viscosity, diffusion coefficient and dye solubilization. The cmc can be determined by measuring one or more of these micelle-dependent physical properties as a function of concentration of the amphipathic molecule. The size and shape of micelles can be determined by dynamic laser light scattering, ultracentrifugation, viscosity and/or low-angle X-ray scattering experiments. Micelles can also exist in liquid crystal phases.

Lipopeptides may be aggregated into micelles by providing a concentration of lipopeptide that is greater than the cmc of the lipopeptide. The cmc is dependent upon the nature of the lipopeptide and the temperature, salt concentration and pH of the aqueous solution comprising the lipopeptide. With respect to the nature of the lipopeptide, the cmc of a lipopeptide is reduced by the addition of $CH_2$ groups to the lipophilic carbon chains. Thus, given the cmc for daptomycin at a particular salt concentration, temperature and pH, then an A-21978 type antibiotic in which the n-decanoyl fatty acid side chain is replaced by n-octanoyl, or -nonanoyl fatty acid side chain will have a higher cmc, while an A-21978 antibiotic in which the n-decanoyl fatty acid side chain of daptomycin is replaced by an n-undecanoyl, n-dodecanoyl, -tridecanoyl or n-tetradecanoyl fatty acid side chain will have a lower cmc relative to daptomycin.

In one embodiment of the invention, the cmc of a lipopeptide may be manipulated, by adding or subtracting a $CH_2$ group to the lipopeptide. In a preferred embodiment, the lipopeptide is A-21978, in which the n-decanoyl fatty acid side chain of daptomycin is replaced by an n-octanoyl, n-nonanoyl, n-undecanoyl, -dodecanoyl, n-tridecanoyl or n-tetradecanoyl fatty acid side chain. In another embodiment, one can calculate the approximate cmc of a lipopeptide following the teachings of the specification. Given the cmc for a lipopeptide such as daptomycin, one may calculate the approximate cmc of a related lipopeptide in which the n-decanoyl fatty acid side chain is replaced by an n-octanoyl, n-nonanoyl, n-undecanoyl, n-dodecanoyl, n-tridecanoyl or n-tetradecanoyl fatty acid side chain. The above may be carried out by methods known by one skilled in the art.

So another preferred embodiment, given the cmc for one lipopeptide, one can calculate the approximate cmc for a lipopeptide that contains a related peptide moiety. In a preferred embodiment, given the cmc for daptomycin and the teachings of the prior art, one may readily determine the cmc for a related lipopeptide such as A54145, a daptomycin-related lipopeptide disclosed in U.S. Pat. Nos. 4,537,717, 4,482,487, Re. 32,311, Re. 32,310, 5,912,226, currently in reissue as U.S. Ser. No. 09/547,357, U.S. Provisional Applications Nos. 60/170,943, 60/170,946 or 60/170,945, filed Dec. 15, 1999, U.S. Provisional Application No. 60/208,222, filed May 30, 2000.

In another embodiment of the invention, the cmc of a lipopeptide is manipulated by changing the temperature of the solution comprising the lipopeptide. The cmc for a lipopeptide usually increases with increasing temperature of the solution. Thus, micelle formation is promoted by decreasing the temperature and is hindered by increasing the temperature. For instance, a solution comprising a lipopeptide may form micelles at 4° C. because at that temperature the cmc is lowered and the lipopeptide concentration is above the cmc; however, the same lipopeptide solution may be monomeric at 20° C. because the cmc has increased with the temperature and the lipopeptide concentration is now below the cmc. Thus, in a preferred embodiment, the concentration of a lipopeptide is higher than the cmc at one temperature and is lower than the cmc at another, higher temperature. In a more preferred embodiment, the lipopeptide is daptomycin or a daptomycin-related molecule, such as those described supra. In an even more preferred embodiment, the lipopeptide is daptomycin.

In another preferred embodiment, the ability to manipulate the formation of micelles of a lipopeptide by using different temperatures to affect the cmc is used in the purification of the lipopeptide. In a more preferred embodiment, the lipopeptide is daptomycin or a related molecule, such as those described supra, in an even more preferred embodiment, the lipopeptide is daptomycin. In another preferred embodiment, the ability to manipulate lipopeptide micelle formation by altering the temperature is used to make pharmaceutical compositions that are micellar under certain temperature conditions and monomeric under other temperature conditions. In a preferred embodiment, the pharmaceutical compositions comprise daptomycin or a daptomycin-related lipopeptide, as described supra. In another preferred embodiment, the pharmaceutical compositions comprise daptomycin.

In a further embodiment of the invention, the addition of an electrolyte is used to decrease the cmc of an ionic lipopeptide. In a preferred embodiment, a salt, such as NaCl, is added to a solution comprising lipopeptide to reduce the repulsion between charged groups in a lipopeptide micelle. In a preferred embodiment, the lipopeptide is daptomycin or a daptomycin-related molecule, such as that described supra. For instance, the peptide moiety of daptomycin contains three aspartic acid residues and an L-threo-3-methylglutamic acid residues (3-MG), all of which would be charged at neutral pH. Thus, addition of an electrolyte, such as NaCl or an equivalent salt, will decrease the cmc of daptomycin. In a preferred embodiment, the salt concentration is at least 100 mM. In a more preferred embodiment, the salt concentration is 150 mM to 300 mM salt, in an even more preferred embodiment the salt is NaCl.

A decrease in the cmc is also observed with addition of an electrolyte for other lipopeptides, such as molecules related to daptomycin that contain aspartic acid residues, 3-MG residues or other charged residues. Therefore, in a preferred embodiment, a salt is added to a solution to decrease the cmc of a daptomycin-related lipopeptide, such as A54145, a daptomycin-related lipopeptide disclosed in U.S. Pat. Nos. 4,537,717, 4,482,487, Re. 32,311, Re. 32,310, 5,912,226, currently in reissue as U.S. Ser. No. 09/547,357, U.S. Provisional Applications Nos. 60/170,943, 60/170,946 or 60/170,945, filed Dec. 15, 1999, U.S. Provisional Application No. 60/208,222, filed May 30, 2000, or an A-21978 antibiotic in which the n-decanoyl fatty acid side chain of daptomycin is replaced by an n-octanoyl, n-nonanoyl, n-undecanoyl, -dodecanoyl, n-tridecanoyl or n-tetradecanoyl fatty acid side chain. In another embodiment, the salt concentration is decreased in order to increase the cmc of an ionic lipopeptide. In a preferred embodiment, the ionic lipopeptide is daptomycin or a daptomycin-related lipopeptide, as described supra.

In another preferred embodiment, the ability to manipulate the formation of micelles of a lipopeptide by altering electrolyte concentration to affect the cmc is used in the purification of the lipopeptide. In a more preferred embodiment, the lipopeptide is daptomycin or a daptomycin-related molecule, such as those described supra. In an even more preferred embodiment, the lipopeptide is daptomycin. In another preferred embodiment, the ability to manipulate lipopeptide micelle formation by electrolyte concentration is used to make pharmaceutical compositions that are micellar at certain electrolyte concentrations and monomeric under other electrolyte concentrations. In a preferred embodiment, the pharmaceutical compositions comprise daptomycin or a daptomycin-related lipopeptide, as described supra. In another preferred embodiment, the pharmaceutical compositions comprise daptomycin.

Figure 15:
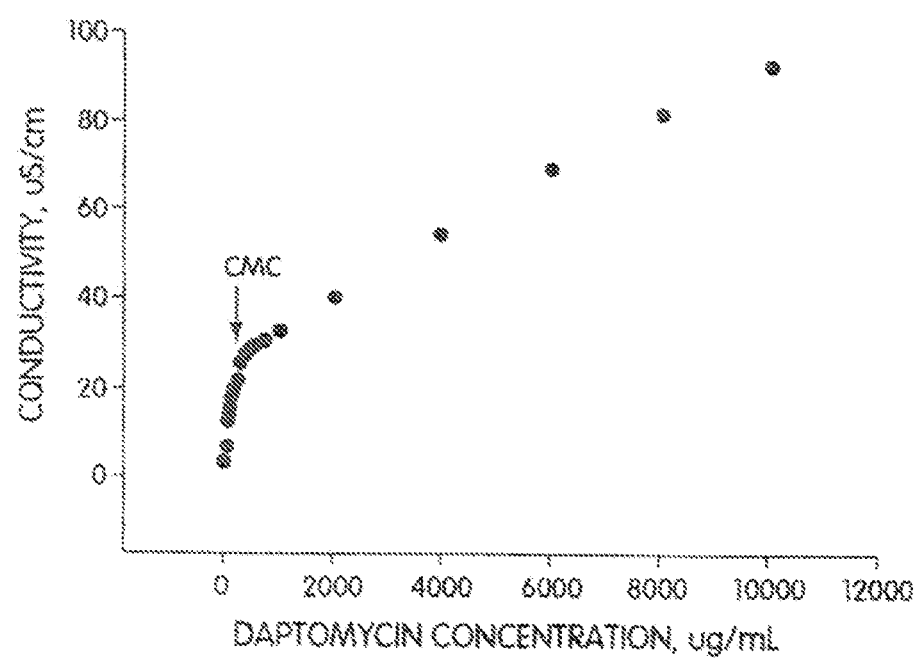
FIG. 15 shows the results of an experiment to determine the critical micellar concentration (cmc) of daptomycin at pH 4.0.

In another embodiment of the invention, the pH of a solution comprising a lipopeptide is manipulated to influence the cmc of the lipopeptide. In a preferred embodiment, the lipopeptide is daptomycin or a daptomycin-related molecule, such as those described supra. In an even more preferred embodiment, the lipopeptide is daptomycin. In one embodiment, the pH is manipulated so that the concentration of a lipopeptide is higher than the cmc at one pH and is lower than the cmc at another pH. For instance, for daptomycin, the cmc at pH 4.0 in water at a temperature of 20-25° C. was much lower than at pH 6.0 or 7.5. At pH 4.0, the cmc is approximately 400 µg/mL under these conditions. See FIG. 15. Further, daptomycin is monomeric even at 150 mg/mL daptomycin at pH 6.5 (wherein the salt concentration is 150 mM to 300 mM NaCl and the temperature is 4° C.). Thus, for daptomycin, the cmc at pH 4.0 is lower than in solutions of either higher pH or lower pH. The change in cmc at different pH levels may also be used for other charged lipopeptides, including lipopeptides that are related to daptomycin, as described supra.

In another preferred embodiment, the ability to manipulate the formation of micelles of a lipopeptide by altering the pH to affect the cmc is used in the purification of the lipopeptide. In a more preferred embodiment, the lipopeptide is daptomycin or a daptomycin-related molecule, such as those described supra. In an even more preferred embodiment, the lipopeptide is daptomycin. In another preferred embodiment, the ability to manipulate lipopeptide micelle formation by pH is used to make pharmaceutical compositions that are micellar at a particular pH and monomeric under another pH. In a preferred embodiment, the pharmaceutical compositions comprise daptomycin or a daptomycin-related lipopeptide, as described supra. In another preferred embodiment, the pharmaceutical compositions comprise daptomycin.

In another aspect of the invention, the lipopeptide may be part of a mixed micelle. A mixed micelle is one in which the lipopeptide forms a micelle with one or more other types of amphipathic molecules. Examples of such amphipathic molecules include, without limitation, medium and long chain fatty acids, phosphoglycerides (phospholipids), sphingomyelin, glycolipids and cholesterol. In one embodiment, medium chain-length alcohols can be incorporated into the micelle, where they reduce electrostatic repulsion and steric hindrance, thus lowering the cmc of the lipopeptide. In another embodiment, the addition of one or more types of amphipathic molecules can be used, to alter the structure of the micelle from a spherical micelle (See FIG. 14, part a) to a lipid bilayer structure (See FIG. 14, part b) or to a liposome structure (See FIG. 14 part c). In general, mixed micelles comprising phospholipids and/or glycolipids will cause a spherical micelle to convert to a lipid bilayer structure, which serve as permeability barriers to ions and most polar molecules.

In another embodiment, the mixed micelle can be formed from two or more different lipopeptides. For instance, the mixed micelle can be formed from daptomycin and another lipopeptide, such as A54145 or a daptomycin-related lipopeptide, as discussed supra. In another embodiment, the mixed micelle may comprise a lipopeptide along with one or more therapeutically useful amphipathic molecules, such as an antibiotic, an anti-inflammatory or an anti-fungal agent, which are known to those having ordinary skill in the art. In a preferred embodiment, the lipopeptide is daptomycin or a daptomycin-related lipopeptide such as A54145, the daptomycin-related lipopeptides disclosed supra, or an A-21978 antibiotic in which the n-decanoyl fatty acid side chain of daptomycin is replaced by an n-octanoyl, n-nonanoyl, n-undecanoyl n-dodecanoyl, n-tridecanoyl or n-tetradecanoyl fatty acid side chain. In a more preferred embodiment, the lipopeptide is daptomycin.

Figure 16:
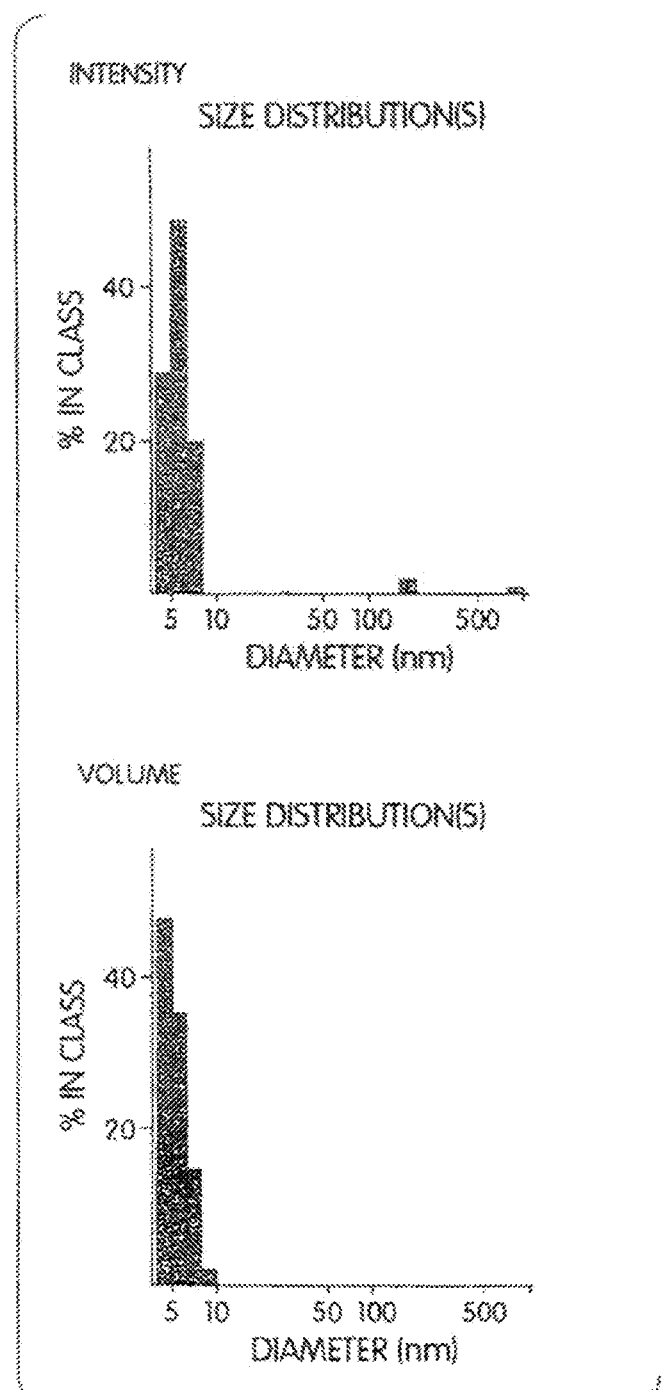
FIG. 16 shows the size distribution of daptomycin micelles by light scatter. The daptomycin micelles have an average size of 5.4 nm (54 A).

In another embodiment of the invention, the micelle, whether mixed or comprising a single type of lipopeptide molecule, comprises a lipopeptide that is therapeutically useful. In a preferred embodiment, the lipopeptide is an antibiotic. In an even more preferred embodiment, the lipopeptide is daptomycin. Daptomycin forms micelles of approximately 5.4 nm (54 Å) at a concentration of 1 mg/mL at pH of approximately 4.0 in water. See FIG. 16.

In another preferred embodiment, the micelles comprise one or more different types of therapeutic substances. In one embodiment, a therapeutic substance can be mixed with the lipopeptide in solution such that a micelle is formed from the lipopeptide and the therapeutic substance is trapped in the hydrophobic interior. In another embodiment, a therapeutic substance is mixed with a lipopeptide and one or more other amphipathic molecules such that a mixed micelle is formed from the lipopeptide and other amphipathic molecules and the therapeutic substance is found in the hydrophobic interior. In a preferred embodiment, the therapeutic substance is an antibiotic, an anti-inflammatory or an anti-fungal agent. In a more preferred embodiment, the therapeutic substance is an antibiotic or antifungal agent disclosed infra. In another preferred embodiment, the therapeutic substance is soluble in a hydrophobic environment but is not soluble in an aqueous solution.

In another embodiment of the invention, the lipopeptides may be formed into liposomes, which are vesicular micelles in which a spherical lipid bilayer surrounds an aqueous interior. See FIG. 14, part c. Liposomes are advantageous for therapeutic uses because they easily fuse with a plasma membrane and can also be used to trap substances in their inner aqueous compartment. The substance can be one that is only soluble in aqueous solutions. In one embodiment, a solution comprising a lipopeptide and another amphipathic molecule can be sonicated to produce liposomes. In another embodiment, the lipopeptide alone can be sonicated to produce liposomes. In a preferred embodiment, the liposome comprises daptomycin or a daptomycin-related lipopeptide such as A54145, a lipopeptide disclosed in U.S. Pat. Nos. 4,537,717, 4,482,487, Re. 32,311, Re. 32,310, 5,912,226, currently in reissue as U.S. Ser. No. 09/547,357, U.S. Provisional Applications Nos. 60/170,943, 60/170,946 or 60/170,945, filed Dec. 15, 1999, U.S. Provisional Application No. 60/208,222, filed May 30, 2000, or A-21978 antibiotic in which the n-decanoyl fatty acid side chain of daptomycin is replaced by an n-octanoyl, n-nonanoyl, n-undecanoyl, -dodecanoyl, n-tridecanoyl or n-tetradecanoyl fatty acid side chain. In a more preferred embodiment, the lipopeptide is daptomycin.

In another preferred embodiment, the liposomes comprise one or more therapeutic substances in their inner aqueous compartments. In a preferred embodiment, the therapeutic substance is an antibiotic, an anti-inflammatory or an anti-fungal agent. In a more preferred embodiment, the therapeutic substance is an antibiotic or antifungal agent disclosed infra. In another preferred embodiment, the therapeutic substance is soluble in aqueous solution. In another preferred embodiment, a pharmaceutical composition comprises the liposome.

In a preferred embodiment, a pharmaceutical composition comprises lipopeptide micelles or lipopeptide micelle containing a therapeutic substance. The lipopeptide micelles may be spherical micelles, mixed micelles or liposomes. Pharmaceutical compositions comprising lipopeptide micelles may minimize local irritation upon injection or when administered intravenously. In one embodiment, the pharmaceutical composition comprises a salt, a buffer to maintain a particular pH and micelles. In a further embodiment, the pharmaceutical composition comprises one or more agents to stabilize the micelles and/or to stabilize the lipopeptide or other therapeutic substance. In one embodiment, the pharmaceutical composition also comprises one or more therapeutic substances. In a preferred embodiment, the therapeutic substance is an antibiotic, an anti-inflammatory or an antifungal agent. In a more preferred embodiment, the therapeutic substance is an antibiotic or antifungal agent disclosed infra. The therapeutic substance can be in addition to the therapeutic substance that is incorporated into the micelle, or can be the therapeutic agent that is incorporated into the micelle.

The pharmaceutical composition can be dried or lyophilized, in which case the micelles are formed when either an aqueous solution, such as water or a buffer is added to the pharmaceutical composition. In a preferred embodiment, the pharmaceutical composition is lyophilized and contains a physiological concentration of salt when reconstituted and a buffer that maintains a pH at which micelles spontaneously form at room temperature when sterile water or other buffer is added. In an even more preferred embodiment, the pharmaceutical composition comprises daptomycin or related lipopeptide, such as A54145, the daptomycin-related lipopeptides disclosed supra, or an A-21978 antibiotic in which the n-decanoyl fatty acid side chain of daptomycin is replaced by an n-octanoyl, n-nonanoyl, n-undecanoyl, n-dodecanoyl, n-tridecanoyl or n-tetradecanoyl fatty acid side chain. In an even more preferred embodiment, the lipopeptide is daptomycin. In another embodiment, the pharmaceutical composition is aqueous. This is preferred when liposomes are used. In a preferred embodiment, the pharmaceutical composition comprises a stabilizing agent for the liposomes.

In another aspect of the invention, the micellar solution is isolated and/or purified. In one embodiment, micelles are isolated from smaller substituents by ultrafiltration. The choice of ultrafiltration membrane will be based upon the size of the micelle. In general a 10,000 NMW or 30,000 NMW membrane will be sufficient to retain micelles while permitting smaller substituents, such as contaminants to flow through. In another embodiment, micelles can be isolated and/or purified by dialysis, density gradient centrifugation or size exclusion chromatography. These methods are well-known in the art. In one embodiment, the micelles are more than 30% pure, where purity is measured as the weight of the micelles compared to the weight of monomeric forms of the lipopeptide or of other molecules. In a preferred embodiment, the micelles are more than 50%, 60%, 70%, 80%, 90% or 95% pure.

In another aspect of the invention, the ability to form lipopeptide micelles and then to disassociate them by altering temperature, pH, electrolyte concentration and/or lipopeptide concentration provides a method for purifying lipopeptides. In one embodiment, the method comprises purifying lipopeptides from low molecular weight contaminants by subjecting lipopeptides to conditions in which the lipopeptides form micelles and then separating the micelles from the contaminants by a size selection technique, such as ultrafiltration or size exclusion chromatography. In another embodiment of the invention, the method comprises concentrating lipopeptides by subjecting lipopeptides to conditions in which the lipopeptides form micelles and then concentrating them by a size selection technique. In a more preferred embodiment, the method comprises both purification and concentration as a single step.

In another embodiment of the invention, the method comprises purifying a lipopeptide from high molecular weight contaminants, including pyrogens (e.g., lipopolysaccharide), by subjecting the lipopeptide to conditions under which the lipopeptide is monomeric and then separating the monomeric lipopeptide solution from the high molecular weight contaminants by a size separation technique. In a preferred embodiment, the size separation technique is ultrafiltration, as discussed supra. In another preferred embodiment, the lipopeptide is daptomycin or related lipopeptide, such as A54145, the daptomycin-related lipopeptides disclosed supra, or an A-21978 antibiotic in which the n-decanoyl fatty acid side chain of daptomycin is replaced by an n-octanoyl, n-nonanoyl, n-undecanoyl, n-dodecanoyl, n-tridecanoyl or n-tetradecanoyl fatty acid side chain. In an even more preferred embodiment, the lipopeptide is daptomycin.

A preferred embodiment of the process chromatography method using micelles to purify daptomycin is described below:

*Streptomyces roseosporus* is fermented with a feed of n-decanoic acid as described supra. After fermentation, the extracellular solution is clarified as described supra.

The clarified preparation is then applied to an anion exchange resin, such as FP-DA 13, as described supra. Daptomycin is eluted from the column with one to three column volumes of an elevated salt buffer containing 300 to 500 mM NaCl.

The eluted daptomycin preparation is adjusted to a pH of 2.5 to 5.0 using an acid. In a preferred embodiment, the acid is dilute phosphoric acid. At pH 2.5 to 4.7, 300 to 500 nM and a temperature of 2-150° C., the daptomycin forms a micelle.

The daptomycin preparation is filtered on a 10,000 to 30,000 NMW ultrafiltration membrane. During ultrafiltration, the daptomycin preparation is washed with a buffer containing 30 mM sodium acetate pH 3.5 and at temperatures of up to 15° C. The initial salt concentration is 300 mM NaCl due to the elution conditions, but the salt concentration decreases as washing continues. Because daptomycin is in micellar form, it is retained on the filter while impurities smaller than the 10,000 to 30,000 (depending upon the filter used), pass through the filter. The daptomycin preparation obtained is approximately 85-90% pure.

As an optional step, the daptomycin preparation may be diluted and its pH raised to 6.5 in order to convert the daptomycin to a monomeric state. The daptomycin preparation is then be passed through a 10,000 NMW ultrafiltration membrane. This optional step decreases pyrogen content significantly.

Methods for Analyzing Daptomycin Purity

Another embodiment of the invention provides analytical methods for measuring the purity of daptomycin.

In the prior art, many of the contaminants that co-purified with daptomycin were unresolved or unidentified because the ability to visualize and measure impurities was limited by the analytical methods and equipment available. See, e.g., U.S. Pat. No. 4,874,843 and Kirsch et al. The development of more sensitive analytical HPLC systems and techniques permits the resolution of a number of contaminants that exist in daptomycin batches prepared by prior art methods. The higher resolution HPLC methods demonstrate that daptomycin as purified by prior art methods is contaminated with previously identified impurities, such as anhydro-daptomycin and β-isomer, and other, previously unknown contaminants that co-purify with daptomycin (and co-elute under the previously established HPLC detection conditions) during the practice of prior art methods. Identification of these contaminants now permits the development of methods designed to eliminate these contaminants.

As discussed above, anhydro-daptomycin and the β-isomer were previously described as impurities that persistently and consistently occurred during preparation of daptomycin. Using the HPLC analyses described here, an additional approximately twelve impurities produced during the production of daptomycin were distinguished, some of which had previously not been identified. These impurities were not removed after purification by the method disclosed in U.S. Pat. No. 4,874,843. At least ten of these compounds have been identified (see, e.g., FIGS. 2-11). Furthermore, at least six of these compounds are not the direct result of the reaction that produces anhydro-daptomycin and the β-isomer form of daptomycin, but rather are compounds produced by other, unrelated, processes that occur during the fermentation or purification of daptomycin. The method of the instant invention, described below, also significantly reduces the levels of a number of these impurities (see Examples).

Any method known in the art may be used to measure the amount of other compounds in a daptomycin preparation. Methods for identifying daptomycin contaminants include, without limitation, mass spectroscopy, infrared spectroscopy, capillary electrophoresis and nuclear magnetic resonance spectroscopy. A preferred method for measuring the amount of other compounds in a daptomycin preparation is HPLC.

Two methods were used to measure daptomycin impurities in the instant invention. The first method is a slightly lower resolution method than the second method. In both methods, a Shimadzu or HP HPLC System with PE Nelson's Turbochrom Software Version 4.1 is used. The "first" resolution method is summarized in Table 1 and the "second" resolution method is summarized in Table 2:

TABLE 1

| | | |
|---|---|---|
| 1. | Solvent Delivery System: | |
| | Mode: | Isocratic pumping |
| | Flow rate: | 1.5 mL/min |
| | Run time: | 30 minutes |
| 2. | Solvent A: | 34% acetonitrile in 0.5% $NH_4H_2PO_4$ at pH 4.5 |
| | Solvent B: | 20% acetonitrile in 0.5% $NH_4H_2PO_4$ at pH 4.5 |
| | The target condition is to retain daptomycin at 15.0 ± 0.5 minutes. Solvent B may be used together with solvent A to adjust the HPLC mobile phase conditions to achieve the desired retention time. | |
| 3. | Autosampler cooler: | 5 (4 to 6) ° C. |
| 4. | Injection volume: | 5 μL to 75 μL (20 μL normal) |
| 5. | Column: | IB-SIL (Phenomenex), C-8, 5μ, 4.6 mm × 250 mm (or equivalent) |
| 6. | Pre-column: | IB-SIL (Phenomenex), C-8, 5μ, 4.6 mm × 30 mm (or equivalent) |
| 7. | Detection wavelength: | 214 nm |
| 8. | Column Temperature: | ambient |
| 9. | Integration: | A computer system or integrator capable of measuring peak area. |

TABLE 2

| | | |
|---|---|---|
| 1. | Solvent Delivery System: | |
| | Mode: | Isocratic pumping |
| | Flow rate: | 1.5 mL/min |
| | Run time: | 75 minutes |
| 2. | Solvent A: | 20% acetonitrile in 0.45% $NH_4H_2PO_4$ at pH 3.25 |
| | Solvent B: | 50% acetonitrile in 0.45% $NH_4H_2PO_4$ at pH 3.25 |
| | The target condition is approximately 35% acetonitrile in 0.45% $NH_4H_2PO_4$ at pH 3.25 (50% Solvent B) to retain | |

TABLE 2-continued daptomycin at 36.0 ± 1.5 minutes; however, the solvent ratio will be used to adjust the HPLC mobile phase composition to achieve the desired retention time.

| | |
|---|---|
| 3. Autosampler cooler: | 5 (4 to 6) ° C. |
| 4. Injection volume: | 5 µL to 75 µL (20 µL normal) |
| 5. Column: | IB-SIL (Phenomenex), C-8, 5µ, 4.6 mm × 250 mm (or equivalent) |
| 6. Pre-column: | IB-SIL (Phenomenex), C-8, 5µ, 4.6 mm × 30 mm (or equivalent) |
| 7. Detection wavelength: | 214 nm |
| 8. Column Temperature: | 25 (22 to 28) ° C. |
| 9. Integration: | A computer system or integrator capable of measuring peak area. |

Purified Lipopeptides, Pharmaceutical Compositions and Methods of Use Thereof

Another object of the instant invention is to provide purified lipopeptides, as well as salts, esters, amides, ethers and protected forms thereof, as well as pharmaceutical formulations comprising purified lipopeptides or its salts. In a preferred embodiment, the lipopeptide is daptomycin or a daptomycin-related lipopeptide, as described supra. A further object of the instant invention is to provide pharmaceutical compositions comprising lipopeptide micelles. In a preferred embodiment, the lipopeptide micelles are micelles comprising daptomycin or one or more daptomycin-related lipopeptides. All reference herein to lipopeptide micelles refers not only to all lipopeptide micelles, but specifically contemplates daptomycin, or related lipopeptide, such as A54145, the daptomycin-related lipopeptides disclosed supra, or an A-21978 antibiotic in which the n-decanoyl fatty acid side chain of daptomycin is replaced by an n-octanoyl, n-nonanoyl, n-undecanoyl, n-dodecanoyl, n-tridecanoyl or n-tetradecanoyl fatty acid side chain. Further, all references herein to lipopeptide micelles specifically contemplates spherical micelles, mixed micelles and liposomes, as discussed supra.

Purified lipopeptides, pharmaceutically acceptable salts thereof, or lipopeptide micelles can be formulated for oral, intravenous, intramuscular, subcutaneous, aerosol, topical or parenteral administration for the therapeutic or prophylactic treatment of diseases particularly bacterial infections. In a preferred embodiment, the purified lipopeptide is purified daptomycin or a daptomycin-related lipopeptide. Reference herein to "purified daptomycin," "purified daptomycin-related lipopeptide" or "purified lipopeptide" includes pharmaceutically acceptable salts thereof. Daptomycin, daptomycin-related lipopeptide or other lipopeptide micelles can be formulated using any pharmaceutically acceptable carrier or excipient that is compatible with daptomycin or with the lipopeptide of interest. See, e.g., Handbook of Pharmaceutical Additives: An International Guide to More than 6000 Products by Trade Name, Chemical, Function, and Manufacturer, Ashgate Publishing Co., eds., M. Ash and I. Ash, 1996; The Merck index: An Encyclopedia of Chemicals, Drugs and Biologicals, ed. S. Budavari, annual; Remington's Pharmaceutical Sciences, Mack Publishing Company, Easton, Pa.; Martindale: The Complete Drug Reference, ed. K. Parfitt, 1999; and Goodman & Gilman's The Pharmaceutical Basis of Therapeutics, Pergamon Press, New York, N.Y., ed. L. S. Goodman, et al.; the contents of which are incorporated herein by reference, for a general description of the methods for administering various antimicrobial agents for human therapy. Purified daptomycin, daptomycin-related lipopeptide or other lipopeptide micelles of this invention can be mixed with conventional pharmaceutical carriers and excipients and used in the form of tablets, capsules, elixirs, suspensions, syrups, wafers, creams and the like. Daptomycin, daptomycin-related lipopeptide or other lipopeptide micelles may be mixed with other therapeutic agents and antibiotics, such as discussed herein. The compositions comprising a compound of this invention will contain from about 0.1 to about 90% by weight of the active compound, and more generally from about 10 to about 30%.

The compositions of the invention can be delivered using controlled (e.g., capsules) or sustained release delivery systems (e.g., bioerodable matrices). Exemplary delayed release delivery systems for drug delivery that are suitable for administration of the compositions of the invention are described in U.S. Pat. No. 4,452,775 (issued to Kent), U.S. Pat. No. 5,239,660 (issued to Leonard), U.S. Pat. No. 3,854,480 (issued to Zaffaroni).

The compositions may contain common carriers and excipients, such as corn starch or gelatin, lactose, sucrose, microcrystalline cellulose, kaolin, mannitol, dicalcium phosphate, sodium chloride and alginic acid. The compositions may contain croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used. It may also be desirable to add a coloring agent to make the dosage form more aesthetic in appearance or to help identify the product.

For oral use, solid formulations such as tablets and capsules are particularly useful. Sustained release or enterically coated preparations may also be devised. For pediatric and geriatric applications, suspensions, syrups and chewable tablets are especially suitable. For oral administration, the pharmaceutical compositions are in the form of, for example, a tablet, capsule, suspension or liquid. The pharmaceutical composition is preferably made in the form of a dosage unit containing a therapeutically-effective amount of the active ingredient. Examples of such dosage units are tablets and capsules. For therapeutic purposes, the tablets and capsules which can contain, in addition to the active ingredient, conventional carriers such as binding agents, for example, acacia gum, gelatin, polyvinylpyrrolidone, sorbitol, or tragacanth; fillers, for example, calcium phosphate, glycine, lactose, maize-starch, sorbitol, or sucrose; lubricants, for example, magnesium stearate, polyethylene glycol, silica, or talc; disintegrants, for example, potato starch, flavoring or coloring agents, or acceptable wetting agents. Oral liquid preparations generally are in the form of aqueous or oily solutions, suspensions, emulsions, syrups or elixirs may contain conventional additives such as suspending agents, emulsifying agents, non-aqueous agents, preservatives, coloring agents and flavoring agents. Oral liquid preparations may comprise lipopeptide micelles or monomeric forms of the lipopeptide. Examples of additives for liquid preparations include acacia, almond oil, ethyl alcohol, fractionated coconut oil, gelatin, glucose syrup, glycerin, hydrogenated edible fats, lecithin, methyl cellulose, methyl or propyl para-hydroxybenzoate, propylene glycol, sorbitol, or sorbic acid.

For intravenous (IV) use, a water soluble form of daptomycin, daptomycin-related lipopeptide or other lipopeptide can be dissolved in any of the commonly used intravenous fluids and administered by infusion. For lipopeptide micelles, the lipopeptide is dissolved in an intravenous formulation under conditions in which the lipopeptide is present at a concentration above its cmc. One having ordinary skill in the art may vary the pH, temperature or salt concentration following the teachings of this invention to obtain an intravenous solution comprising lipopeptide micelles. Further, one may sonicate the lipopeptide solution in order to obtain lipopeptide liposomes. Intravenous formulations may include carriers, excipients or stabilizers including, without limitation, calcium, human serum albumin, citrate, acetate, calcium chloride, carbonate, and other salts. Intravenous fluids include, without limitation, physiological saline or Ringer's solution. Daptomycin or daptomycin-related lipopeptide also may be placed in injectors, cannulae, catheters and lines.

Formulations for parenteral administration can be in the form of aqueous or non-aqueous isotonic sterile injection solutions or suspensions. These solutions or suspensions can be prepared from sterile powders or granules having one or more of the carriers mentioned for use in the formulations for oral administration. Lipopeptide micelles may be particularly desirable for parenteral administration. The compounds can be dissolved in polyethylene glycol, propylene glycol, ethanol, corn oil, benzyl alcohol, sodium chloride, and/or various buffers. For intramuscular preparations, a sterile formulation of a lipopeptide compound or a suitable soluble salt form of the compound, for example the hydrochloride salt, can be dissolved and administered in a pharmaceutical diluent such as Water-for-Injection (WFI), physiological saline or 5% glucose.

Lipopeptide micelles may be particularly desirable for parenteral administration because they are likely to cause no local irritation at the site of injection. Without wishing to be bound by any theory, it is likely that lipopeptide micelles will cause less local irritation than monomeric lipopeptides because the lipid tails, which might cause irritation upon injection, will be sequestered in the interior of the micelle, while the peptide nucleus, which is less likely to cause local irritation than the lipid tail, will be exposed to the tissue. Lipopeptide micelles may be prepared for intramuscular and parenteral preparations by following the teachings of this invention to obtain a preparation comprising lipopeptide micelles. Further, one may sonicate the lipopeptide solution in order to obtain lipopeptide liposomes. A suitable insoluble form of the compound also may be prepared and administered as a suspension in an aqueous base or a pharmaceutically acceptable oil base, e.g., an ester of a long chain fatty acid such as ethyl oleate.

Injectable depot forms may be made by forming microencapsulated matrices of the compound in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in microemulsions that are compatible with body tissues.

For topical use the compounds and micelles of the present invention can also be prepared in suitable forms to be applied to the skin, or mucus membranes of the nose and throat, and can take the form of creams, ointments, liquid sprays or inhalants, lozenges, or throat paints. Such topical formulations further can include chemical compounds such as dimethylsulfoxide (DMSO) to facilitate surface penetration of the active ingredient. For topical preparations, a sterile formulation of daptomycin, daptomycin-related lipopeptide, suitable salt forms thereof, or a lipopeptide micelle may be administered in a cream, ointment, spray or other topical dressing. Topical preparations may also be in the form of bandages that have been impregnated with purified daptomycin, daptomycin-related lipopeptide or a lipopeptide micelle composition.

For application to the eyes or ears, the compounds of the present invention can be presented in liquid or semi-liquid form formulated in hydrophobic or hydrophilic bases as ointments, creams, lotions, paints or powders.

For rectal administration the compounds of the present invention can be administered in the form of suppositories admixed with conventional carriers such as cocoa butter, wax or other glyceride.

For aerosol preparations, a sterile formulation of purified daptomycin or a daptomycin-related lipopeptide or salt form of the compound may be used in inhalers, such as metered dose inhalers, and nebulizers. A sterile formulation of a lipopeptide micelle may also be used for aerosol preparation. Aerosolized forms may be especially useful for treating respiratory infections, such as pneumonia and sinus-based infections.

Alternatively, the compounds of the present invention can be in powder form for reconstitution in the appropriate pharmaceutically acceptable carrier at the time of delivery. If the powder form is to be reconstituted as lipopeptide micelles, the powder may comprise a buffer and/or salt such that reconstitution with a particular quantity of sterile water or saline will cause the lipopeptide to form micelles. Alternatively, the powder form may contain instructions regarding the quantity and type of pharmaceutically acceptable carrier is to be used to reconstitute the lipopeptide in order to obtain micelles. In another embodiment, the unit dosage form of the compound can be a solution of the compound, a salt thereof, or a lipopeptide micelle in a suitable diluent in sterile, hermetically sealed ampules. The concentration of the compound in the unit dosage may vary, e.g. from about 1 percent to about 50 percent, depending on the compound used and its solubility and the dose desired by the physician. If the compositions contain dosage units, each dosage unit preferably contains from 50-500 mg of the active material. For adult human treatment, the dosage employed preferably ranges from 100 mg to 3 g. per day, depending on the route and frequency of administration.

In a further aspect, this invention provides a method for treating an infection, especially those caused by gram-positive bacteria, in humans and other-animals. The term "treating" is used to denote both the prevention of an infection and the control of an established infection after the host animal has become infected. An established infection may be one that is acute or chronic. The method comprises administering to the human or other animal an effective dose of a compound of this invention. An effective dose is generally between about 0.1 and about 25 mg/kg purified daptomycin, daptomycin-related lipopeptide or pharmaceutically acceptable salts thereof. The daptomycin or daptomycin-related lipopeptide may be monomeric or may be part of a lipopeptide micelle. A preferred dose is from about 1 to about 25 mg/kg of purified daptomycin or daptomycin-related lipopeptide or pharmaceutically acceptable salts thereof. A more preferred dose is from about 1 to 12 mg/kg purified daptomycin or a pharmaceutically acceptable salt thereof.

In one embodiment, the invention provides a method for treating an infection, especially those caused by gram-positive bacteria, in a subject with a therapeutically-effective amount of daptomycin or other antibacterial lipopeptide. The daptomycin or antibacterial lipopeptide may be monomeric or in a lipopeptide micelle. Exemplary procedures for delivering an antibacterial agent are described in U.S. Pat. No. 5,041,567, issued to Rogers and in PCT patent application number EP94/02552 (publication no. WO 95/05384), the entire contents of which documents are incorporated in their entirety herein by reference. As used herein the phrase "therapeutically-effective amount" means an amount of daptomycin or antibacterial lipopeptide according to the present invention that prevents the onset, alleviates the symptoms, or stops the progression of a bacterial infection. The term "treating" is defined as administering, to a subject, a therapeutically-effective amount of a compound of the invention, both to prevent the occurrence of an infection and to control or eliminate an infection. The term "subject", as described herein, is defined as a mammal, a plant or a cell culture. In a preferred embodiment, a subject is a human or other animal patient in need of lipopeptide compound treatment.

The lipopeptide antibiotic compound can be administered as a single daily dose or in multiple doses per day. The treatment regime may require administration over extended periods of time, e.g., for several days or for from two to four weeks. The amount per administered dose or the total amount administered will depend on such factors as the nature and severity of the infection, the age and general health of the patient, the tolerance of the patient to the antibiotic and the microorganism or microorganisms involved in the infection. A method of administration is disclosed in U.S. Ser. No. 09/406,568, filed Sep. 24, 1999, herein incorporated by reference, which claims the benefit of U.S. Provisional Application Nos. 60/101,828, filed Sep. 25, 1998, and 60/125,750, filed Mar. 24, 1999.

The methods of the present invention comprise administering purified daptomycin or other lipopeptide antibiotic, or pharmaceutical compositions thereof to a patient in need thereof in an amount that is efficacious in reducing or eliminating the gram-positive bacterial infection. The daptomycin or lipopeptide antibiotic may be either monomeric or may be present in a lipopeptide micelle. The antibiotic may be administered orally, parenterally, by inhalation, topically, rectally, nasally, buccally, vaginally, or by an implanted reservoir, external pump or catheter. The antibiotic may be prepared for opthalmic or aerosolized uses. Purified daptomycin, lipopeptide antibiotic, or pharmaceutical compositions thereof also may be directly injected or administered into an abscess, ventricle or joint. Parenteral administration includes subcutaneous, intravenous, intramuscular, infra-articular, intrasynovial, cisternal, intrathecal, intrahepatic, intralesional and intracranial injection or infusion. In a preferred embodiment, daptomycin or other lipopeptide is administered intravenously, subcutaneously or orally.

The method of the instant invention may be used to treat a patient having a bacterial infection in which the infection is caused or exacerbated by any type of gram-positive bacteria. In a preferred embodiment, purified daptomycin, daptomycin-related lipopeptide, other lipopeptide or pharmaceutical compositions thereof are administered to a patient according to the methods of this invention. In another preferred embodiment, the bacterial infection may be caused or exacerbated by bacteria including, but not limited to, methicillin-susceptible and methicillin-resistant staphylococci (including *Staphylococcus aureus, Staphylococcus epidermidis, Staphylococcus haemolyticus, Staphylococcus hominis, Staphylococcus saprophyticus*, and coagulase-negative staphylococci), glycopeptide intermediary-susceptible *Staphylococcus aureus* (GISA), penicillin-susceptible and penicillin-resistant streptococci (including *Streptococcus pneumoniae, Streptococcus pyogenes, Streptococcus agalactiae, Streptococcus avium, Streptococcus bovis, Streptococcus laetis, Streptococcus sangius* and Streptococci Group C, Streptococci Group G and viridans streptococci), enterococci (including vancomycin-susceptible and vancomycin-resistant strains such as *Enterococcus faecalis* and *Enterococcus faecium*), *Clostridium difficile, Clostridium clostridiiforme, Clostridium innocuum, Clostridium perfringens, Clostridium ramosum, Haemophilus influenzae, Listeria monocytogenes, Corynebacterium jeikeium, Bifidobacterium* spp., *Eubacterium aerofaciens, Eubacterium lentum, Lactobacillus acidophilus, Lactobacillus casei, Lactobacillus plantarum, Lactococcus* spp., *Leuconostoc* spp., *Pediococcus, Peptostreptococcus anaerobius, Peptostreptococcus asaccaroylyticus, Peptostreptococcus magnus, Peptostreptococcus micros, Peptostreptococcus prevotii, Peptostreptococcus productus, Propionibacterium acnes*, and *Actinomyces* spp.

The antibacterial activity of daptomycin against classically "resistant" strains is comparable to that against classically "susceptible" strains in in vitro experiments. In addition, the minimum inhibitory concentration (MIC) value for daptomycin against susceptible strains is typically 4-fold lower than that of vancomycin. Thus, in a preferred embodiment, purified daptomycin, daptomycin-related lipopeptide antibiotic, or pharmaceutical compositions thereof are administered according to the methods of this invention to a patient who exhibits a bacterial infection that is resistant to other antibiotics, including vancomycin. In addition, unlike glycopeptide antibiotics, daptomycin exhibits rapid, concentration-dependent bactericidal activity against gram-positive organisms. Thus, in a preferred embodiment, purified daptomycin, lipopeptide antibiotic, or pharmaceutical compositions thereof are administered according to the methods of this invention to a patient in need of rapidly acting antibiotic therapy.

The method of the instant invention may be used for a grant-positive bacterial infection of any organ or tissue in the body. These organs or tissue include, without limitation, skeletal muscle, skin, bloodstream, kidneys, heart, lung and bone. The method of the invention may be used to treat, without limitation, skin and soft tissue infections, bacteremia and urinary tract infections. The method of the invention may be used to treat community acquired respiratory infections, including, without limitation, otitis media, sinusitis, chronic bronchitis and pneumonia, including pneumonia caused by drug-resistant *Streptococcus pneumoniae* or *Haemophilus influenzae*. The method of the invention also may be used to treat mixed infections that, comprise different types of gram-positive bacteria, or which comprise both gram-positive and grain-negative bacteria, including aerobic, caprophilic or anaerobic bacteria. These types of infections include intra-abdominal infections and obstetrical/gynecological infections. The methods of the invention may be used in step-down therapy for hospital infections, including, without limitation, pneumonia, intra-abdominal sepsis, skin and soft tissue infections and bone and joint infections. The method of the invention also may be used to treat an infection including, without limitation, endocarditis, nephritis, septic arthritis and osteomyelitis. In a preferred embodiment, any of the above-described diseases may be treated using purified daptomycin, lipopeptide antibiotic, or pharmaceutical compositions thereof. Further, the diseases may be treated using daptomycin or lipopeptide antibiotic in either a monomeric or micellar form.

Daptomycin, daptomycin-related lipopeptide or other lipopeptide may also be administered in the diet or feed of a patient or animal. If administered as part of a total dietary intake, the amount of daptomycin or other lipopeptide can be less than 1% by weight of the diet and preferably no more than 0.5% by weight. The diet for animals can be normal foodstuffs to which daptomycin or lipopeptide can be added or it can be added to a premix.

The method of the instant invention may also be practiced while concurrently administering one or more antifungal agents and/or one or more antibiotics other than daptomycin or other lipopeptide antibiotic. Co-administration of an antifungal agent and an antibiotic other than daptomycin or another lipopeptide antibiotic may be useful for mixed infections such as those caused by different types of gram-positive bacteria, those caused by both gram-positive and gram-negative bacteria, or those that caused by both bacteria and fungus. Furthermore, daptomycin or other lipopeptide antibiotic may improve the toxicity profile of one or more co-administered antibiotics. It has been shown that administration of daptomycin and an aminoglycoside may ameliorate renal toxicity caused by the aminoglycoside. In a preferred embodiment, an antibiotic and/or antifungal agent may be administered concurrently with purified daptomycin, other lipopeptide antibiotic, or in pharmaceutical compositions comprising purified daptomycin or another lipopeptide antibiotic.

Co-administration of another therapeutic agent with daptomycin or another lipopeptide antibiotic may be performed using daptomycin or lipopeptide antibiotic in either a monomeric or micellar form. As discussed supra, spherical lipopeptide micelles can be used to help solubulize agents that exhibit low aqueous solubility. Further, lipopeptide liposomes can be used to trap agents that are soluble in aqueous media inside the vesicle of the liposomes. By following the teachings of the specification, one having ordinary skill in the art would be able to make lipopeptide micelles comprising therapeutic agents, such as anti-inflammatory agents, antifungal agents and other antibiotics.

Antibacterial agents and classes thereof that may be coadministered with daptomycin or other lipopeptide antibiotics include, without limitation, penicillins and related drugs, carbapenems, cephalosporins and related drugs, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomycin, tetracyclines, vancomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomycin, glycopeptide, glycylcylcline, ketolides, oxazolidinone; imipenem, amikacin, netilmicin, fosfomycin, gentamicin, ceftriaxone. Ziracin, LY 333328, CL 331002, HMR 3647, Linezolid, Synercid, Aztreonam, and Metronidazole, Epiroprim, OCA-983, GV-143233, Sanfetrinem sodium, CS-834. Biapenem, A-99058.1, A-165600, A-179796, KA 159, Dynemiein A. DX8739, DU 6681; Cefluprenam, ER 35786, Cefoselis, Sanfetrinem celexetil, HGP-31, Cefpirome, HMR-3647, RU-59863, Mersacidin, KP 736. Rifalazil; Kosan, AM 1732, MEN 10700, Lenapenem, BO 2502A, NE-1530, PR 39, K130, OPC 20000, OPC 2045, Veneprim, PD 138312, PD 140248, CP 111905, Sulopenem, ritipenam acoxyl, RO-65-5788, Cyclothialidine, Sch-40832, SEP-132613, micacocidin A. SB-275833, SR-15402, SUN A0026, TOC 39, carumonam, Cefozopran, Cefetamet pivoxil, and T 3811.

In a preferred embodiment, antibacterial agents that may be co-administered with daptomycin according to this invention include, without limitation, imipenem, amikacin, netilmicin, fosfomycin, gentamicin, ceftriaxone, teicoplanin, Ziracin, LY 333328, CL 331002, HMR 3647, Linezolid, Synercid, Aztreonam, and Metronidazole.

Antifungal agents that may be co-administered with daptomycin or other lipopeptide antibiotic include, without limitation, Caspofungen, Voriconazole, Sertaconazole, IB-367, FK-463, LY-303366, Sch-56592, Sitafloxacin, DB-289 polyenes, such as Amphotericin, Nystatin, Primaricin; azoles, such as Fluconazole, Itraconazole, and Ketoconazole; allylamines, such as Naftifine and Terbinafine; and anti-metabolites, such as Flucytosine. Other antifungal agents include without limitation, those disclosed in Fostel et al., Drug Discovery Today 5:25-32 (2000), herein incorporated by reference. Fostel et al. disclose antifungal compounds including Corynecandin, Mer-WF3010, Fusacandins, Artrichitin/LL 15G256γ, Sordarins, Cispentacin, Azoxybacillin, Aureobasidin and Khafrefungin.

Daptomycin or other lipopeptide antibiotic, including daptomycin-related lipopeptides, may be administered according to this method until the bacterial infection is eradicated or reduced. In one embodiment, daptomycin or other lipopeptide is administered for a period of time from 3 days to 6 months. In a preferred embodiment, daptomycin or other lipopeptide is administered for 7 to 56 days. In a more preferred embodiment, daptomycin or other lipopeptide is administered for 7 to 28 days. In an even more preferred embodiment, daptomycin or other lipopeptide is administered for 7 to 14 days. Daptomycin or other lipopeptide may be administered for a longer or shorter time, period if it is so desired.

In order that this invention may be more fully understood, the following examples are set forth. These examples are for the purpose of illustration only and are not to be construed as limiting the scope of the invention in any way.

EXAMPLE 1

A fermentation culture of *S. roseosporus* NRRL Strain 15998 is conducted in a controlled decanoic acid feed fermentation at levels that optimize the production of the antibiotic while minimizing the production of contaminants. The residual decanoic acid feed is measured by gas chromatography and the target residual level is 10 ppm decanoic acid from the start of induction (approximately at hour 30) until harvest. Centrifugation of the culture and subsequent analysis of the clarified broth are used to measure the production of daptomycin by HPLC. The harvest titer is typically between 2.1 and 2.6 grams per liter of fermentation broth.

The fermentation is harvested either by microfiltration using a Pall-Sep or by full commercial-scale centrifugation and depth filter. The clarified broth is applied to an anion exchange resin, Mitsubishi FP-DA 13, washed with 30 mM NaCl at pH 6.5 and eluted with 300 mM NaCl at pH 6.0-6.5. Alternatively, the FP-DA 13 column is washed with 60 mM NaCl at pH 6.5 and eluted with 500 mM NaCl at pH 6.0-6.5. The eluate is applied to a HIC resin, HP-20ss, washed with 30% acetonitrile, and eluted with 35% acetonitrile at pH 4.0-5.0. Alternatively, the HIC resin is washed with 45% isopropyl alcohol and eluted with 55-60% isopropyl alcohol. The eluate is applied to FP-DA 13 resin and washed and eluted as before. The final anion exchange step reduces solvent by one third or more. Reverse osmosis diafiltration and concentration at pH 1.5-2.5 is performed using an 0.2 µm filter and the daptomycin preparation is frozen. A final reverse osmosis diafiltration is conducted with Water-For-Injection (WFI) to wash daptomycin and adjust its concentration prior to sterile-filling. Vials or bulk quantities of daptomycin are then lyophilized.

EXAMPLE 2

Daptomycin was produced in a fermentation culture of *S. roseosporus* and partially purified Daptomycin (9.9 Kg) was purified by micro filtration from 5500 liters of fermentation broth by the method described in U.S. Pat. No. 4,885,243. The partially purified daptomycin was further purified by the method described in U.S. Pat. No. 4,874,843, and resulted in a bulk daptomycin preparation with a purity of 91%. The daptomycin preparation contained fourteen impurities by HPLC analysis (see Example 10). The daptomycin preparation was applied to a Poros P150 anion exchange resin (PE Biosystems) in Tris buffer pH 7.0 containing 6M urea and allowed to bind to the resin. The resin was washed with three column volumes of buffer prior to initiation of a NaCl gradient in the same buffer. Alternatively, the contaminants can be effectively removed from the column with a fixed salt level of 30 mM NaCl. The elution of purified daptomycin from the resin occurred at approximately 300 mM NaCl during a 0 to 1000 mM NaCl gradient. Daptomycin eluted from the column was greater than 99% pure as measured by the "first" HPLC method. The purified daptomycin contained only one detectable daptomycin contaminant. Anhydro-daptomycin and β-isomer were undetectable (less than 0.01% contamination). The level of the unidentified contaminant was greater than 0.1% and less than 0.5%.

EXAMPLE 3

A bulk daptomycin preparation with a purity of 91% was prepared as described in Example 2. The product was applied to a Poros D50 anion exchange resin (PE Biosystems) in an acetate buffer pH 7.0 containing 6M urea. The Poros D50 resin was washed and eluted in the same manner as described in Example 2. Daptomycin eluted from the column was 96.92% pure as measured by the "second" HPLC method. The product of this invention contained only two of the initial fourteen impurities (less than 0.5% contamination). Anhydro-daptomycin could not be detected in the purified daptomycin preparation (less than 0.01% contamination and with precise quantitation at less than 0.05%).

EXAMPLE 4

A fermentation broth containing daptomycin was produced as described in Example 2. The fermentation broth was clarified by microfiltration. The clarified product was extracted with 20% n-butanol or iso-butanol at pH 4.5 (one part butanol to four parts clarified solution). Re-extraction of the clarified solution was performed to achieve a yield of partially purified daptomycin of greater than 90% of the total daptomycin in the clarified solution. Daptomycin was recovered from the butanol phase by the addition of a pH 6.5 aqueous buffer in a volume that is one-half or more of the volume of butanol to extract daptomycin from the butanol phase into the aqueous phase. The butanol extraction step resulted in a partially purified daptomycin preparation that was purified 5-fold and concentrated 10-fold relative to the clarified solution.

The aqueous daptomycin preparation was then purified by the method disclosed in U.S. Pat. No. 4,874,845, resulting in daptomycin that was 91% pure. Daptomycin contained fourteen impurities. The product was applied to a Poros D50 resin in a Tris buffer at pH 7.0 containing 6M urea. The resin was washed with three bed volumes of Tris buffer at pH 7.0 containing 6M urea prior to initiation of a NaCl gradient from 0 to 1000 mM in the same buffer. Elution of purified daptomycin from the resin occurred at approximately 300 mM NaCl. Daptomycin was 98% pure as measured by the "second" HPLC method.

EXAMPLE 5

Daptomycin is fermented as described in Example 2. The 5500 liters fermentation broth contains 13 Kg daptomycin. The fermentation broth is directly extracted with 20% n-butanol at pH 4.5, which partitions daptomycin into the butanol. Re-extractions of the fermentation broth with butanol are performed to achieve a yield of greater than 90% of the total daptomycin in the fermentation broth. The butanol phase is extracted with an aqueous acetate buffer at pH 6.5, resulting in daptomycin that is purified 5-fold (35%) and concentrated 10-fold relative to the fermentation broth. The aqueous daptomycin is microfiltered by the method described in U.S. Pat. No. 4,885,243, then purified by the method of U.S. Pat. No. 4,874,843. This method results in daptomycin with a purity of approximately 91%. Daptomycin contains 14 impurities by the HPLC method used at the time of the prior art. The product is applied to a Poros D50 resin column in a acetate buffer at pH 7.0 containing 6M urea. Washing and elusion of the resin is performed as indicated in Example 2. The product of the chromatographic step is approximately 98% to 99% pure as measured by the second HPLC method.

EXAMPLE 6

Daptomycin was produced in a fermentation culture of *S. roseosporus* except a reduced residual decanoic acid feed was used in order to improve the quality of the fermentation to about 10% purity when clarified by microfiltration or centrifugation. The decanoic acid level was monitored and periodically adjusted to maintain the residual decanoic acid levels at less than 50 ppm and preferably between 1 and 10 ppm during fermentation. The fermentation broth was microfiltered by the method described in U.S. Pat. No. 4,885,243 to produce 12.1 Kg partially purified daptomycin from 5500 liters of fermentation broth. Clarified fermentation broth was bound to the anion exchanger, FP-DA 13 (Mitsubishi) in acetate buffer at neutral pH, washed in acetate buffer containing 30 mM NaCl, and subsequently eluted with acetate buffer at 300 mM NaCl. This anion exchange step produced daptomycin with a purity of greater than 70%. This partially purified daptomycin was further purified by the method of U.S. Pat. No. 4,874,843 with the modification that HP-20ss resin was used. Specifically, the partially purified daptomycin was loaded on HP-20ss in acetate buffer containing 10% acetonitrile, washed with acetate buffer containing 30% acetonitrile and eluted with 40% acetonitrile in acetate buffer, resulting in daptomycin with a purity of about 94 to 96% as measured by the "second" HPLC method. The product is subjected to modified buffer enhanced anion exchange chromatography using Poros D50 resin as described in Example 5. Daptomycin is greater than 99% pure and contains only two of the fourteen impurities produced by methods described in the prior art.

EXAMPLE 7

A daplomycin preparation with a purity of 93% was prepared as described in Example 2. The product was applied to a Poros P150 resin (PE Biosystems) in an acetate buffer pH 6.0 containing 2M urea. The Poros P150 resin was washed with three column volumes of the buffer. Daptomycin was eluted from the resin using a 0 to 400 mM NaCl gradient in the acetate buffer pH 6.0 containing 2M urea. Daptomycin eluted between 150 and 300 mM NaCl. Daptomycin eluted from the column was 99.0 to 99.5% pure as measured by the "first" HPLC method. Daptomycin contained trace amounts of four impurities that were less than 1% of the total of daptomycin. Anhydro-daptomycin could not be detected in the purified daptomycin preparation (less than 0.02% contamination).

EXAMPLE 8

A daptomycin preparation with a purity of 93% was prepared as described in Example 2. The product was applied to a Poros P150 resin (PE Biosystems) in an acetate buffer pH 6.0 containing 2M urea. The column was washed with six column volumes of 60 mM NaCl in acetate buffer pH 6.0 containing 2M urea (the "wash buffer"). The wash buffer may vary from 50-75 mM NaCl. The wash removes virtually all anhydro-daptomycin. Daptomycin is eluted with sixteen column volumes of 250 mM NaCl in-acetate buffer pH 6.0 containing 2M urea. Daptomycin is 98.5 to 99.5% pure as measured by the "first" HPLC method.

EXAMPLE 9

A daptomycin preparation as described in Example 2 was prepared using a method that significantly reduced the concentration of solvent required to perform the HP-20ss chromatography. Unexpectedly, the solvent for elution of daptomycin, 40% acetonitrile or 55-60% isopropyl alcohol, was reduced to 12% and 25%, respectively, when HP-20ss chromatography was conducted at neutral pH rather than acidic pH as described in U.S. Pat. No. 4,874,843. In a preferred embodiment, pH shift can be used to recycle the HP-20SS resin without solvent removal.

After elution from a FP-DA13 column at pH 6.5-7.0, daptomycin is loaded on an equilibrated HP-20ss column, such as one that has been equilibrated in 60 mM acetate, pH 6.6. The column is washed with five to eight column bed volumes (CSV) wash buffer. An exemplary wash buffer is 5% isopropyl alcohol/60 mM acetate, pH 6.6. Daptomycin is eluted from the column with elution buffer. An exemplary elution buffer is two to three CBV 25% isopropyl alcohol/60 mM acetate pH 6.6. The column is stripped with strip buffer. In one embodiment, the column is stripped with one CSV 40% isopropyl alcohol/60 mM acetate pH 6.6-7.0. The daptomycin solution is adjusted to pH 3.5-4.0 and is reloaded on to the HP-20ss column in order to further enhance purity. In one embodiment, the daptomycin eluted front the HP-20ss column at pH 6.5 is adjusted to pH 3.5 using 0.25M phosphoric acid. The daptomycin solution is reloaded on the previously stripped HP-20ss column that has been equilibrated in 60 mM acetate, pH 3.5. The column is washed with a pH adjusting buffer such that the pH is 6.5. An exemplary pH adjusting buffer is five to eight CBV 5% isopropyl alcohol/60 mM acetate, pH 6.6. The daptomycin is eluted with elution buffer and may be further purified by anion exchange or other purification methods, if desired. The HP-20ss column is stripped with strip buffer and cleaned prior to reuse. An exemplary cleaning process includes washing with three CBV 0.5M NaOH, washing with one CBV water, and then washing with 0.25M phosphoric acid prior to equilibration. The column may be stored in 0.5M NaOH.

EXAMPLE 10

Figure 12:
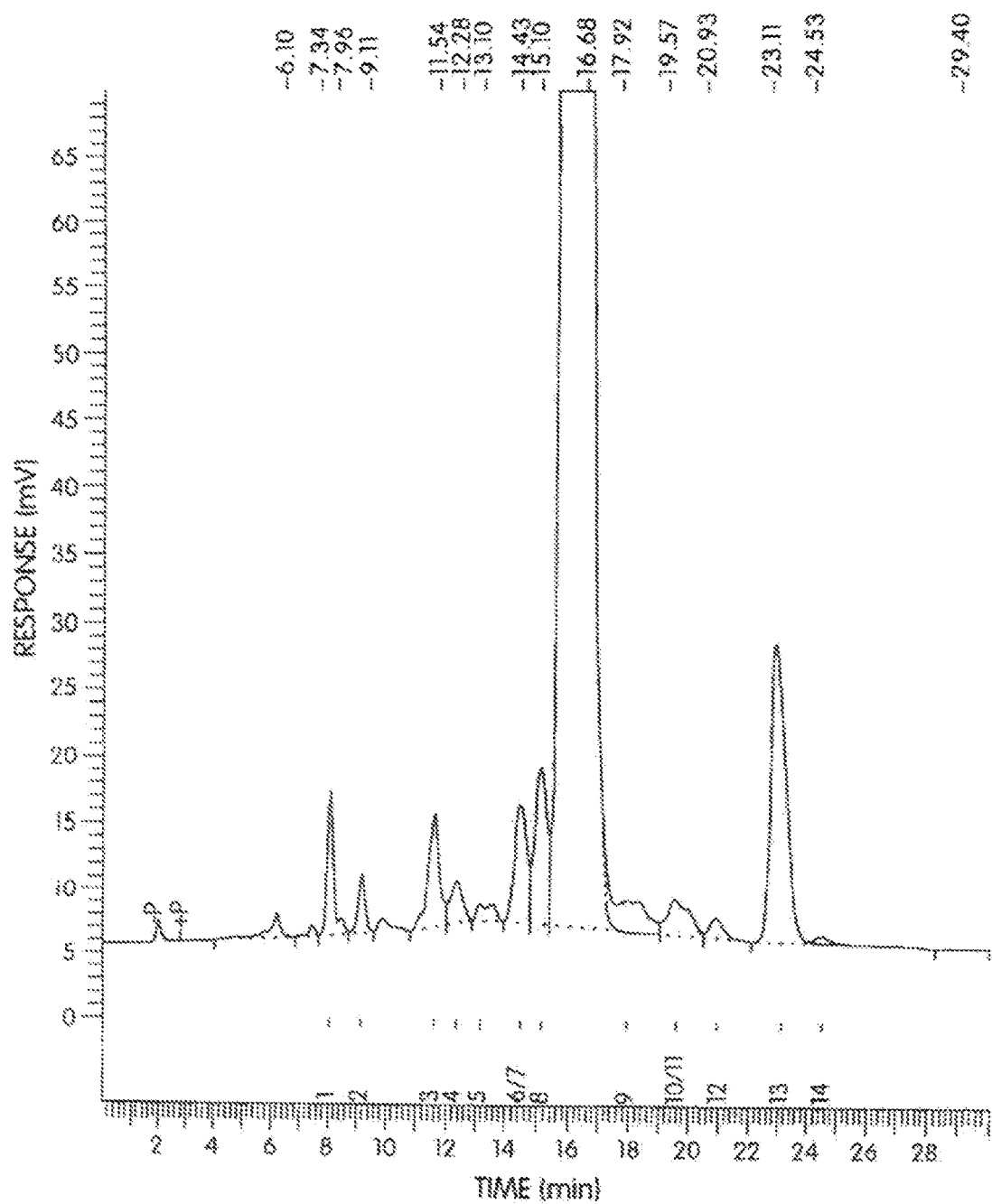
FIG. 12 shows an HPLC chromatogram for a bulk preparation of daptomycin, including impurities 1 to 14.

Bulk daptomycin prepared as described in Example 2 was characterized via semi-preparative HPLC and characterized by liquid chromatography/mass spectroscopy (LC/MS) using both positive and negative ion modes. An impurity profile of the bulk daptomycin prior to chromatography on the Poros P150 anion exchange resin is shown in Table 3 and a chromatogram of the bulk daptomycin preparation is shown in FIG. 12.

TABLE 3

| Impurity ID | Retention Time | Observed MW | Lilly ID | Cubist ID | % of Total Area by HPLC |
| --- | --- | --- | --- | --- | --- |
| 1 | 7.96 | 1638 | LY212218 | CB-131012 | >0.5%, <1.0% |
| 2 | 9.11 | 1638 | | CB-131011 | <0.5%, >0.1% |
| 3 | 11.54 | 745 | LY213928 | CB-131008 | >0.5%, <1.0% |
| 4 | 12.28 | 1624 | | CB-131006 | <0.5%, >0.1% |
| 5 | 13.10 | 1618 | | Unknown-1 | <0.5%, >0.1% |
| 6 | 14.43 | 587 | LY213827 | CB-130989 | >0.5%, <1.0% |
| 7 | 14.43 | 1606 | | CB-131005 | >0.5%, <1.0% |
| 8 | 15.10 | 1620 | LY213846 | CB-131010 | >1.0%, <4.0% |
| Daptomycin | 16.68 | 1620 | LY146032 | CB-109187 | >90% |
| 9 | 17.92 | 874 | | Unknown-2 | <0.5%, >0.1% |
| 10 | 19.57 | 1810 | | Unknown-3 | <0.5%, >0.1% |
| 11 | 19.57 | 1635 | | Unknown-4 | <0.5%, >0.1% |
| 12 | 20.93 | 859 | | CB-131009 | <0.5%, >0.1% |
| 13 | 23.11 | 1602 | LY178480 | CB-130952 | >1.0, <4.0% |
| 14 | 24.53 | 1634 | LY109208 | CB-131078 | <0.1 |

Figure 4:
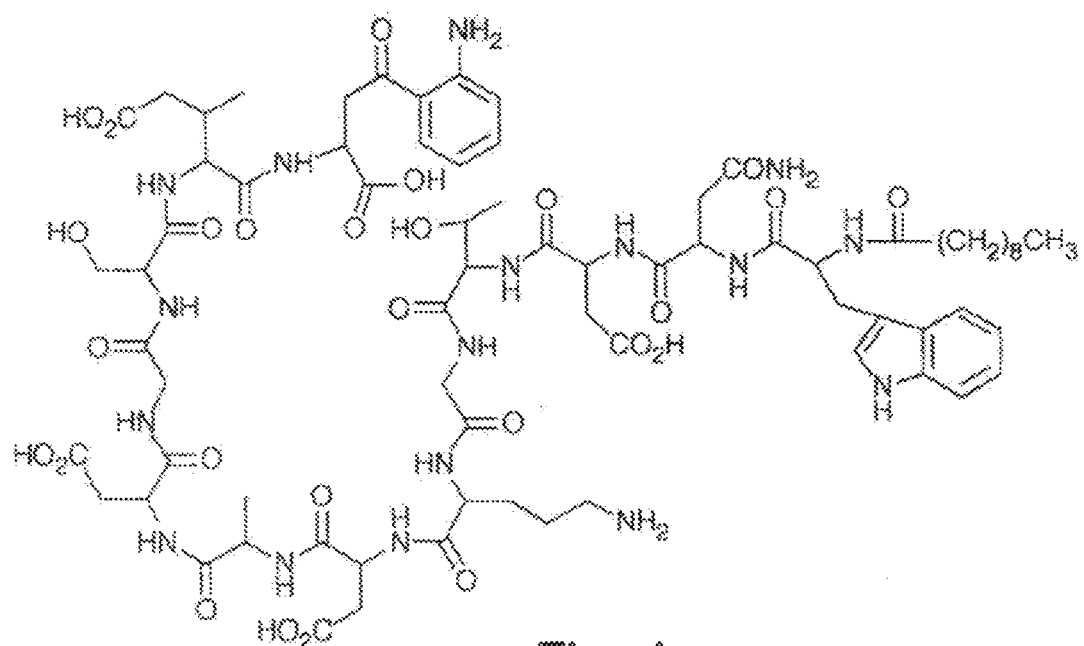
FIG. 4 shows the proposed structure of impurity 1, CB-131012 (previously identified as LY212218).

Impurity 1 (CB-131012), which elutes at approximately 7.96 minutes, (MW: 1638) is proposed to be a lactone hydrolysis product of daptomycin (FIG. 4). The results seem to match LY212218 as previously identified by Lilly as a decyl ring opened derivative of daptomycin.

Figure 5:
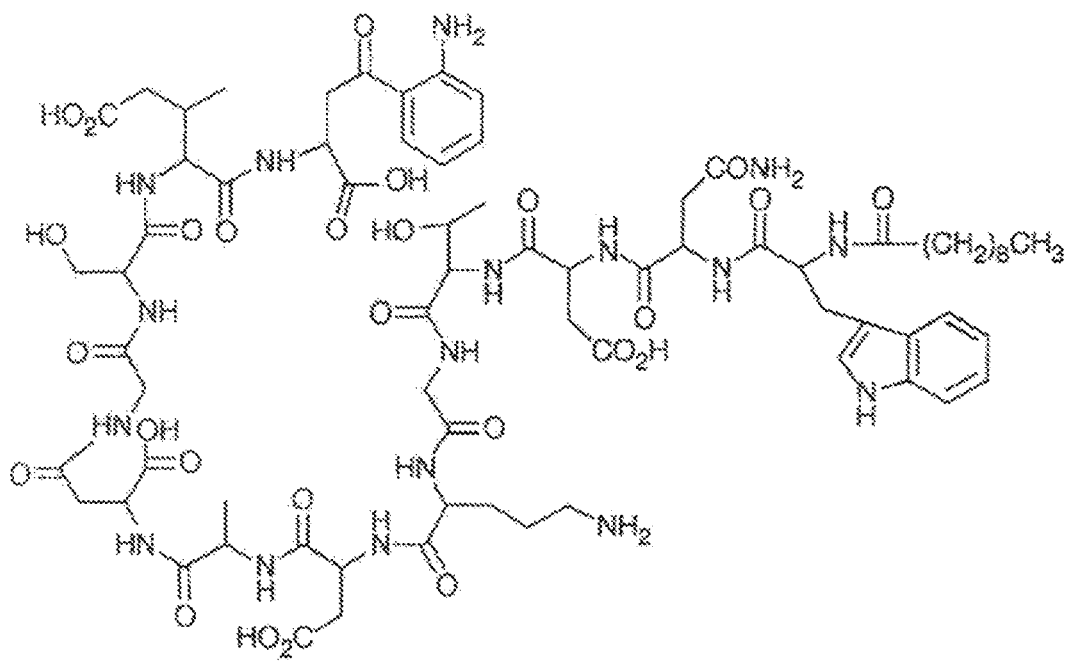
FIG. 5 shows the proposed structure of impurity 2, CB-131011.

Impurity 2 (CB-131011), which elutes at approximately 9.11 minutes, (MW: 1638) is also proposed to be a lactone hydrolysis product of the β-isomer (FIG. 5).

Figure 6:
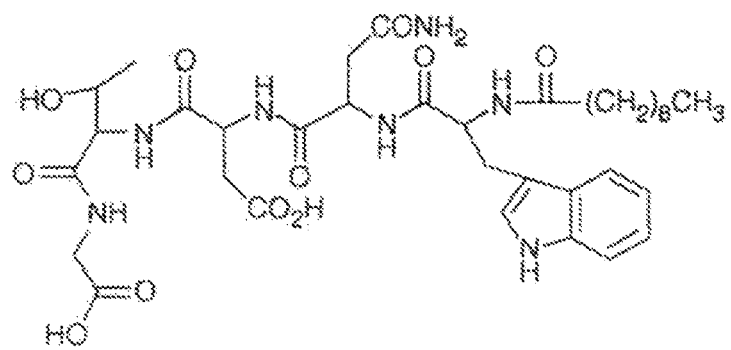
FIG. 6 shows the proposed structure of impurity 3, CB-131008 (previously identified as LY213928).

Impurity 3 (CB-131008), which elutes at approximately 11.54 minutes, (MW: 745) is proposed to be a linear lipopeptide consisting of a five amino acid chain containing tryptophan, asparagine, aspartate, threonine and glycine with a decanoic acid chain (FIG. 6). This result seems to match LY213928 as previously identified by Lilly.

Figure 7:
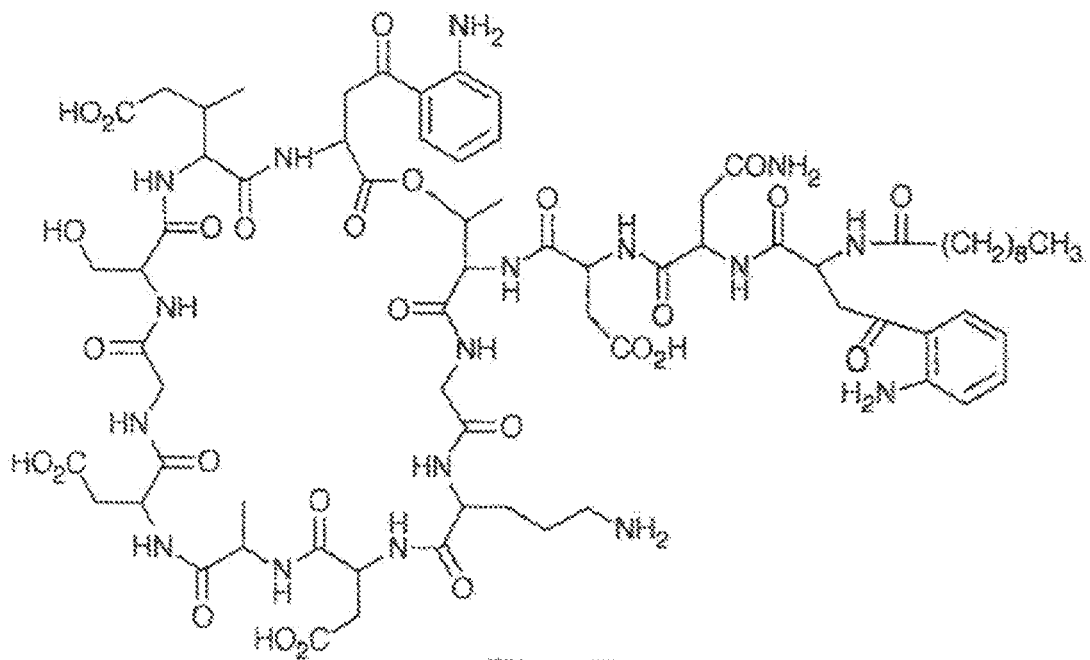
FIG. 7 shows the proposed structure of impurity 4, CB-131006.
Figure 8:
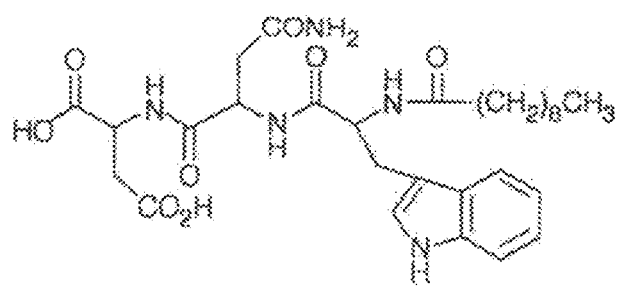
FIG. 8 shows the proposed structure of impurity 6, CB-130989 (previously identified as LY213827).

Impurity 4 (CB-131006), which elutes at approximately 12.28 minutes, (MW: 1624) is proposed to be an oxidative analog of daptomycin in which the amino acid tryptophan has been oxidized to kynuric acid (FIG. 7).

Impurity 5, which elutes at approximately 13.10 minutes, (MW: 1618) has not yet been assigned a structure.

Figure 9:
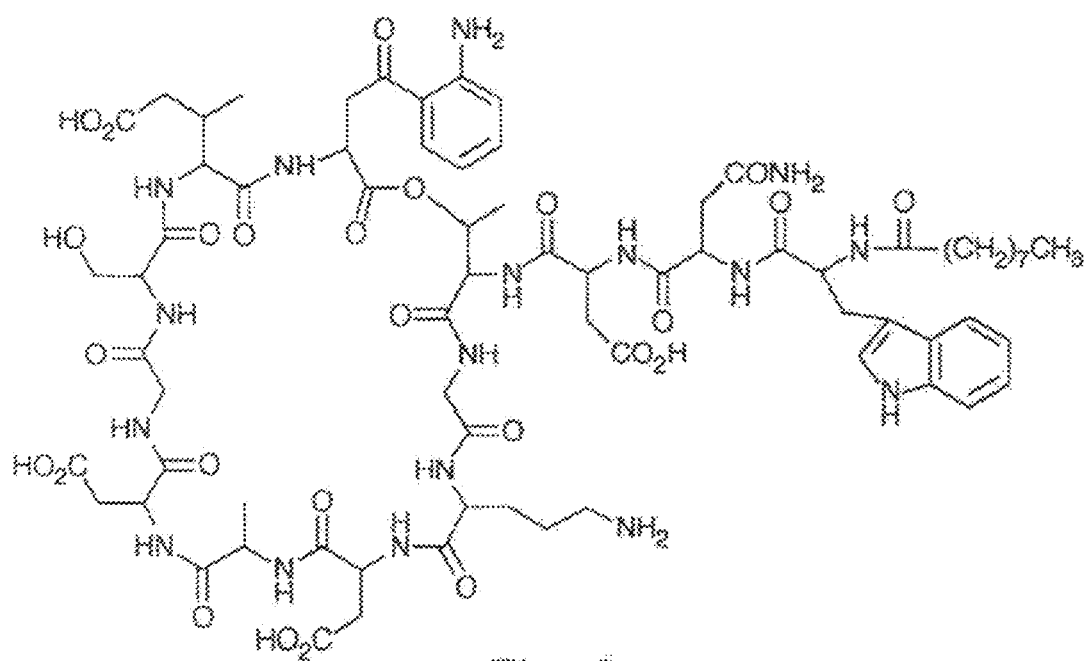
FIG. 9 shows the proposed structure of impurity 7, CB-131005.

Impurity 6 (CB-130989) and Impurity 7 (CB-131005) co-elute at approximately 14.43 minutes. CB-130989 (MW: 587) seems to match LY213827 a linear lipopeptide consisting of a three amino acid chain of tryptophan, asparagine and aspartate with a decanoic acid chain (FIG. 8), as previously identified by Lilly. CB-131005 (MW: 1606) corresponds to a daptomycin analog in which the decanoic acid lacks one methyl group (FIG. 9).

Figure 2:
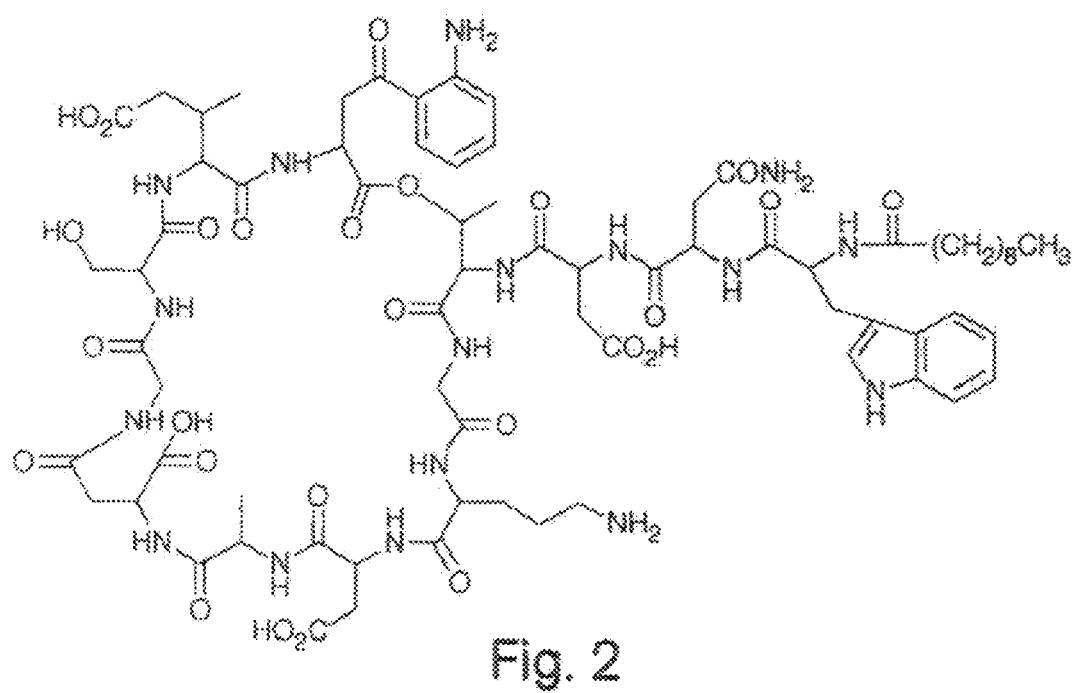
FIG. 2 shows the structure of impurity 8, CB-131010 (previously identified as the β-isomer, LY213846).

Impurity 8 (CB-131010), elutes at approximately 15.10 minutes, (MW: 1620) matches LY213846 (β-isomer) as previously identified by Lilly (FIG. 2). Levels of β-isomer are greater than 1%.

Impurity 9, which elutes at approximately 17.92 minutes (MW: 874), has not yet been assigned a structure.

Impurity 10 and 11, which co-elute at approximately 19.57 minutes, have not been assigned a structure.

Figure 10:
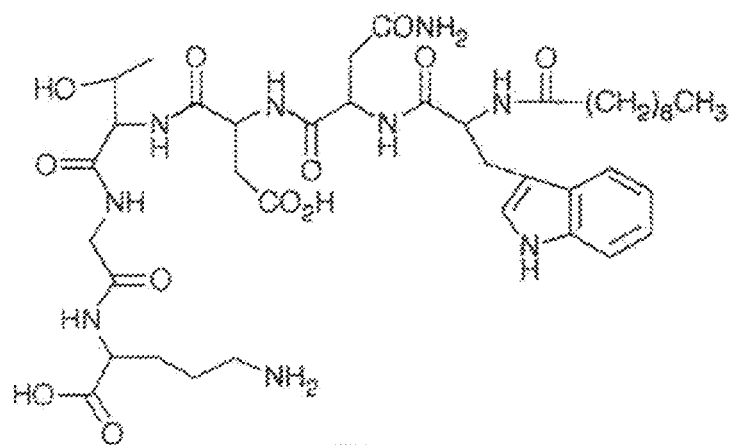
FIG. 10 shows the proposed structure of impurity 12, CB-131009.

Impurity 12 (CB-131009), which elutes at 20.93 minutes (MW: 859), is proposed to be a linear lipopeptide consisting of a six amino acid chain of tryptophan, asparagine, aspartate, threonine, glycine and ornithine with a decanoic acid chain (FIG. 10).

Impurity 13 (CB-130952), which elutes at approximately 23.11 minutes (MW: 1602), is proposed to be anhydro-daptomycin (FIG. 3), and appears to be the same as LY178480. Levels of anhydro-daptomycin are greater than 1%.

Figure 11:
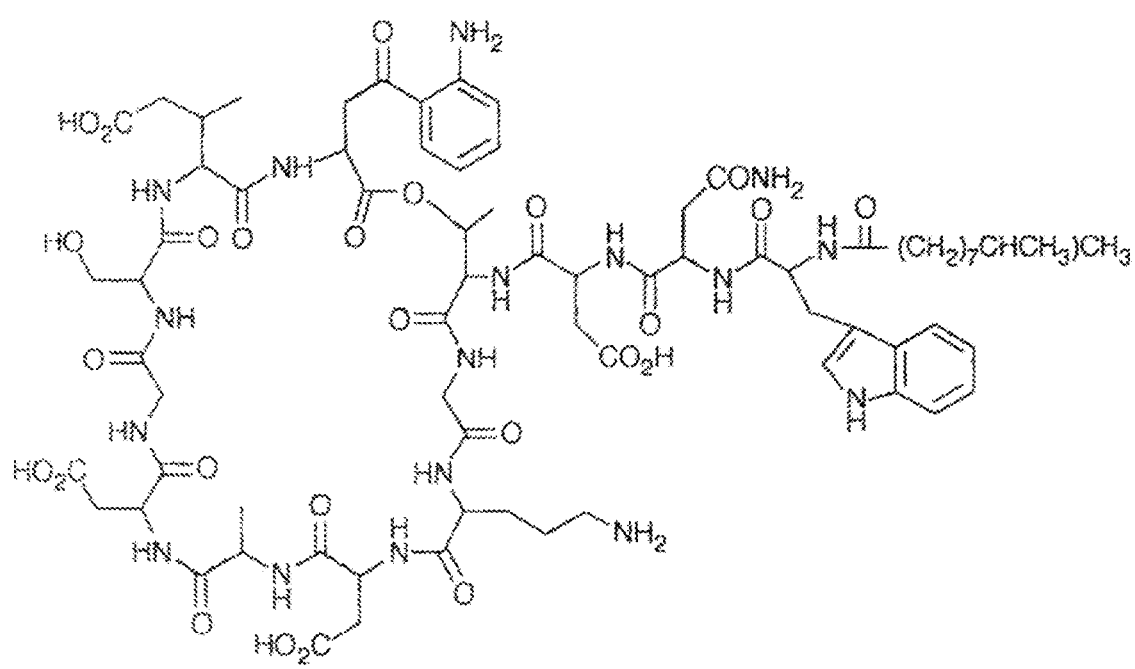
FIG. 11 shows the proposed structure of impurity 14, CB-131078 (previously identified as LY109208).

Impurity 14 (CB-131078), which elutes at approximately 24.53 minutes (MW: 1634), appears to be the same as LY109208, previously identified by Lilly as a daptomycin analog containing an extra methyl group in the decanoic acid chain (FIG. 11).

Figure 13:
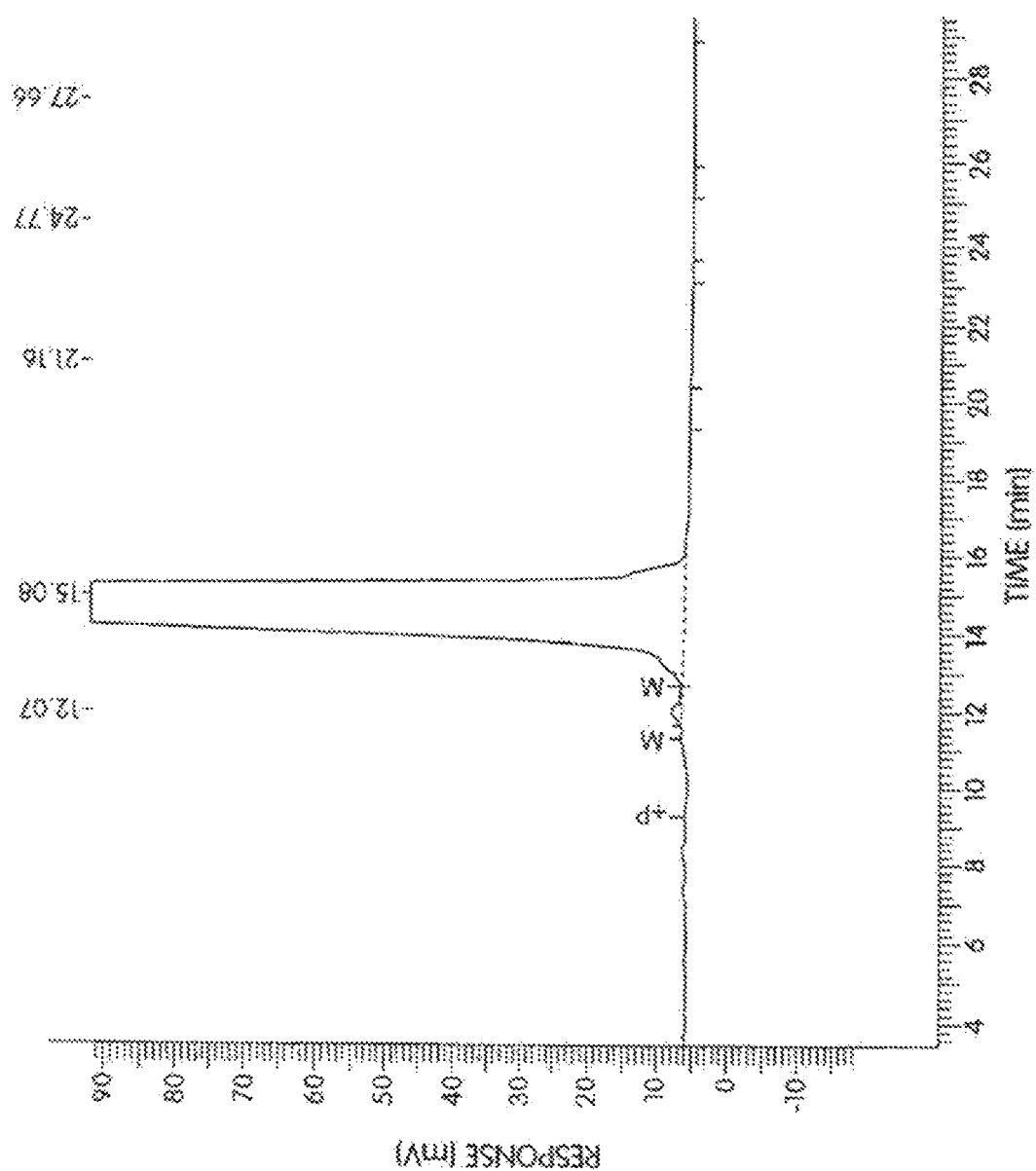
FIG. 13 shows an HPLC chromatogram for a preparation of daptomycin after purification on a Poros P150 resin.

The bulk daptomycin may be purified on Poros P150 as described above in Examples 2 or 7-8 or may be purified on Poros D50 as described above in Examples 3-5. After purification on Poros P150 as described in Example 2, a chromatogram (FIG. 13) shows that daptomycin purity is greater than 99.0%, with β-isomer and anhydro-daptomycin below the level of detection (less than 0.05% of total). There is one unidentified impurity which is present in a quantity of greater than 0.1% but less than 0.5%.

EXAMPLE 11

A fermentation culture of *S. roseosporus* NRRL Strain 15998 is conducted in a controlled decanoic acid feed fermentation at levels that optimize the production of the antibiotic while minimizing the production of contaminants. The residual decanoic acid feed is measured by gas chromatography and the target residual level is 10 ppm decanoic acid from the start of induction (approximately at hour 30) until harvest. Centrifugation of the culture and subsequent analysis of the clarified broth are used to measure the production of daptomycin by HPLC. The harvest titer is typically between 1.0 and 3.0 grams per liter of fermentation broth.

The fermentation is harvested either by microfiltration using a Pall-Sep or by full commercial-scale centrifugation and depth filter. The clarified broth is applied to an anion exchange resin. Mitsubishi FP-DA 13, washed with 30 mM NaCl at pH 6.5 and eluted with 300 mM NaCl at pH 6.0-6.5. Alternatively, the FP-DA 13 column is washed with 60 mM NaCl at pH 6.5 and eluted with 500 mM NaCl at pH 6.0-6.5. The pH is adjusted to 3.0 to 4.8 and the temperature is adjusted to 2-15° C. Under these conditions, daptomycin forms a micelle. The micellar daptomycin solution is purified by washing the micellar preparation while it is retained on a ultra filter using a 10,000 NMW filter (AG Technology Corp. UF hollow fiber or equivalent) in any configuration. The daptomycin micelles are retained by the filter, but a large number of impurities are eliminated because they pass through the 10,000 NMW filter. Ultrafiltration of daptamycin micelles increases daptomycin purity from approximately 40% to 80% or greater.

The eluate is applied to a HIC resin, HP-20ss, washed with 30% acetonitrile, and eluted with 35% acetonitrile at pH 4.0-5.0. Alternatively, the HIC resin is washed with 20-30% isopropyl alcohol and eluted with 30-40% isopropyl alcohol at pH 3.5-6.5. Under these conditions of increased solvent and a higher pH of 6.0-7.5, daptomycin reverts to a single, non-micelle state. The eluate is applied to FP-DA 13 resin column and washed and eluted as before. The final anion exchange step reduces solvent by one third or more. Reverse osmosis diafiltration and concentration at pH 1.5-2.5 is performed using an 0.2 μm filter and the daptomycin preparation is frozen. A final reverse osmosis diafiltration is conducted with Water-For-Injection (WFI) to wash daptomycin and adjust its concentration prior to sterile-filling. Vials or bulk quantities of daptomycin are then lyophilized.

EXAMPLE 12

Lyophilized daptomycin purified as described in any of the above-described examples, such as that described in Example 11, is reconstituted in physiologic saline (approximately 140 mM NaCl) at a pH of 4.0-5.0. Under these conditions, daptomycin is present as a micelle, and can be used for injection or intravenous, parenteral, oral or topical administration.

EXAMPLE 13

Daptomycin is produced by fermentation and clarified from the broth by microfiltration as described in Example 11. The clarified broth is applied to an anion exchange resin, Mitsubishi FP-DA 13, washed with 30 mM NaCl at pH 6.5 and eluted with 3.00 mM NaCl at pH 6.0-6.5 to give a daptomycin preparation that is approximately 40% pure. The eluate is adjusted to pH 3.5 with dilute phosphoric acid such that virtually all of the daptomycin forms micelles. The micelle preparation is loaded on a 10,000 NMW ultrafiltration membrane. The daptomycin preparation is washed with 30 mM sodium acetate pH 3.5 and at temperatures of up to 15° C. The reduction in volume and washing lowers the contamination level, which results in an 85% pure daptomycin preparation. The daptomycin preparation can be further purified using any of the methods described herein.

EXAMPLE 14

Daptomycin is produced by fermentation, clarified from the broth by microfiltration, and fractionated on the FP-DA 13 resin as described in Example 11. The eluate is adjusted to pH 3.5 with dilute phosphoric acid such that virtually all of the daptomycin forms micelles. The micelle preparation is loaded on a 10,000 NMW ultrafiltration membrane. The daptomycin preparation is washed with 30 mM sodium acetate pH 3.5 and at temperatures of up to 15° C. The reduction in volume and washing lowers the contamination level, which results in an 80-90% pure daptomycin preparation. The daptomycin preparation can be further purified using any of the methods described herein.

EXAMPLE 15

Daptomycin is produced by fermentation and clarified from the broth using microfiltration as described in Example 11. The preparation is purified using hydrophobic interaction chromatography, as described in U.S. Pat. No. 4,874,843, herein incorporated by reference. In this method, repeated column chromatography on HP-20 and HP-20ss resin is used. Daptomycin purity is 93% with visible impurities on HPCC chromatographs and measurable pyrogen. The product is diluted in water and its pH was adjusted to pH 6.5 with NaOH or the equivalent. The daptomycin preparation is filtered through a 10,000 NMW ultrafiltration membrane. Under these conditions, daptomycin is monomeric and passes through the ultrafiltration membrane. The resulting product remains 93% pure, but several impurities that had been present at 0.1-0.2% are removed by the ultrafiltration membrane. In addition, pyrogen content is reduced to undetectable levels.

EXAMPLE 16

A daptomycin preparation of approximately 93% purity is prepared as described in Example 15, The daptomycin preparation is converted to a micellar state by lowering the pH to 4.7 with HCl or equivalent and chilling the daptomycin preparation to 2-5° C. The product is concentrated from 400 liters to three liters and to a final concentration of approximately 100 mg/ml by filtration on a 10,000 NMW ultra filtration membrane. Under these conditions, daptomycin is retained by the membrane. This results in a large increase in daptomycin concentration. The purity is approximately 93%.

EXAMPLE 17

A daptomycin preparation is prepared as described in Example 16. Vials are filled with approximately 250 mg daptomycin and lyophilized. The daptomycin is reconstituted in 50 ml of sterile 150 mM saline at a pH of 4.0-5.0 for administration to a human or animal patient. The dose of daptomycin that is administered will depend upon the nature of the infection, the age and weight of the patient, and the species of animal. At a pH of 4.0-5.0 in for 50 mM saline, the daptomycin will be present in a micellar state, which is soluble and suitable, for intravenous, intramuscular or parenteral injection. The formulation will minimize any local irritation due to the lipopeptide nature of daptomycin.

EXAMPLE 18

Daptomycin micelles were produced using daptomycin at a concentration of 1.0 mg/mL in water at pH 4.0 at 25° C. The size of a daptomycin micelle was measured using a Zetasizer™ (Malvern Instruments, Model 3000 HS). The count rate of 36.3, the cell type was a capillary cell, the detection angle (deg) was 90°, and the wavelength (nm) was 633. Results indicated that the diameter of the micelle was 54 A, which is about twice the diameter of a single monomeric daptomycin molecule. See FIG. 18.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A pharmaceutical composition comprising daptomycin of greater than or about 93% purity relative to impurities 1-14 defined by peaks 1-14 shown in FIG. 12, the daptomycin being obtained by a process comprising the step of forming an aggregate comprising daptomycin, wherein the daptomycin is free of pyrogen, and wherein the composition:
 optionally comprises a pharmaceutically acceptable carrier or excipient; and
 comprises daptomycin micelles when reconstituted in at least one solution.

2. The composition of claim 1, wherein the daptomycin is greater than 93% pure.

3. The composition of claim 1, wherein the daptomycin is greater than 95% pure.

4. The composition of claim 1, wherein the daptomycin is free of one to five impurities selected from impurities 1 to 14 defined by peaks 1-14 shown in FIG. 12.

5. The composition of claim 1, wherein at least one of impurities 2, 4, 5, 6, and 12 is present in an amount of no more than 0.1%.

6. The composition of claim 1, wherein impurity 3 is present in an amount of no more than 0.5%.

7. The composition of claim 1, wherein the daptomycin is obtained by a process comprising:
 a) subjecting a daptomycin solution to conditions forming a daptomycin aggregate;
 b) separating the daptomycin aggregate from low molecular weight contaminants; and
 c) subjecting the daptomycin aggregate to conditions in which the daptomycin aggregate dissociates into daptomycin monomers.

8. The composition of claim 7, wherein the daptomycin aggregate of step b) is separated from the low molecular weight contaminants by a size selection technique chosen from ultrafiltration and size exclusion chromatography.

9. The composition of claim 8, further comprising separating the daptomycin monomers obtained from step c) from high molecular weight contaminants.

10. The composition of claim 9, wherein the daptomycin monomers are separated from the high molecular weight contaminants by a size selection technique chosen from ultrafiltration and size exclusion chromatography.

11. The composition of claim 7, wherein the aggregate is a micelle.

12. The composition of claim 10, wherein the daptomycin is free of one to five impurities selected from impurities 1 to 14 defined by peaks 1-14 shown in FIG. 12.

13. The composition of claim 10, wherein at least one of impurities 2, 4, 5, 6, and 12 is present in an amount of no more than 0.1%.

14. The composition of claim 12, wherein impurity 3 is present in an amount of no more than 0.5%.

15. A pharmaceutical composition comprising daptomycin of greater than or about 93% purity relative to impurities 1-14 defined by peaks 1-14 shown in FIG. 12, the daptomycin being obtained by a process comprising the steps of forming a daptomycin aggregate, converting the daptomycin aggregate to monomers, and one or more steps selected from the group consisting of anion exchange chromatography and hydrophobic interaction chromatography, wherein the daptomycin is free of pyrogen, and wherein the composition:
 optionally comprises a pharmaceutically acceptable carrier or excipient; and
 comprises daptomycin micelles when reconstituted in at least one solution.

16. The composition of claim 15, wherein the daptomycin is greater than 93% pure.

17. The composition of claim 15, wherein the daptomycin is greater than 95% sure.

18. The composition of claim 15, wherein the daptomycin is free of one to five impurities selected from impurities 1 to 14 defined by peaks 1-14 shown in FIG. 12.

19. The composition of claim 15, wherein at least one of impurities 2, 4, 5, 6, and 12 is present in an amount of no more than 0.1%.

20. The composition of claim 15, wherein impurity 3 is present in an amount of no more than 0.5%.

21. A pharmaceutical composition comprising daptomycin of greater than or about 93% purity relative to impurities 1-14 defined by peaks 1-14 shown in FIG. 12, wherein the daptomycin is free of pyrogen, and wherein the composition:
 optionally comprises a pharmaceutically acceptable carrier or excipient; and
 comprises daptomycin micelles when reconstituted in at least one solution.

22. The composition of claim 21, wherein the daptomycin is greater than 93% pure.

23. The composition of claim 21, wherein the daptomycin is greater than 95% pure.

24. The composition of claim 21, wherein the daptomycin is free of one to five impurities selected from impurities 1 to 14 defined by peaks 1-14 shown in FIG. 12.

25. The composition of claim 21, wherein at least one of impurities 2, 4, 5, 6, and 12 is present in an amount of no more than 0.1%.

26. The composition of claim 21, wherein impurity 3 is present in an amount of no more than 0.5%.

27. A method for treating a bacterial infection in a human patient in need thereof, comprising administering a therapeutically effective amount of the pharmaceutical composition of claim 11.

28. A method for treating a bacterial infection in a human patient in need thereof, comprising administering a therapeutically effective amount of the pharmaceutical composition of claim 15.

29. A method for treating a bacterial infection in a human patient in need thereof, comprising administering a therapeutically effective amount of the pharmaceutical composition of claim 21.

30. The composition of claim 1, wherein the daptomycin is greater than 97% pure.

31. The composition of claim 15, wherein the daptomycin is greater than 97% pure.

32. The composition of claim 21, wherein the daptomycin is greater than 97% pure.

* * * * *